(12) United States Patent
Fleiszig et al.

(10) Patent No.: US 7,332,470 B2
(45) Date of Patent: Feb. 19, 2008

(54) METHODS AND COMPOSITIONS FOR TREATING OCULAR DISEASE

(75) Inventors: Suzanne Fleiszig, Oakland, CA (US); David J. Evans, Oakland, CA (US); Robert Sack, Brookhaven, NY (US)

(73) Assignees: The Regents of the University of California, Oakland, CA (US); The Research Foundation of State University of New York, Albany, NY (US)

( * ) Notice: Subject to any disclaimer, the term of this patent is extended or adjusted under 35 U.S.C. 154(b) by 374 days.

(21) Appl. No.: 10/823,819

(22) Filed: Apr. 14, 2004

(65) Prior Publication Data

US 2004/0229802 A1 Nov. 18, 2004

Related U.S. Application Data

(60) Provisional application No. 60/462,913, filed on Apr. 15, 2003.

(51) Int. Cl.
*A61K 38/00* (2006.01)
*A61K 31/74* (2006.01)
*C07K 14/00* (2006.01)

(52) U.S. Cl. .......................... 514/2; 514/887; 514/954; 530/350; 530/396; 424/78.02; 424/78.04; 424/78.05; 424/78.07

(58) Field of Classification Search .................... 514/2, 514/887, 954; 530/350, 396; 424/78.02, 424/78.04, 78.05, 78.07; 435/810
See application file for complete search history.

(56) References Cited

U.S. PATENT DOCUMENTS

| 5,242,902 | A | 9/1993 | Murphy et al. ................ 514/12 |
| 6,110,708 | A | 8/2000 | Wakamiya .................. 435/69.7 |
| 2003/0022831 | A1 | 1/2003 | Rothbard et al. .............. 514/12 |

FOREIGN PATENT DOCUMENTS

WO   WO 01/80633 A2   11/2001

OTHER PUBLICATIONS

Fleiszig et al. Modification of *Pseudomonas aeruginosa* Interactions with Corneal Epithelial Cells by Human Tear Fluid, Jul. 2003, Infection and Immunity, vol. 71, No. 7, pp. 3866-3874.*

Ni et al. Surfactant Protein D Is Present in Human Tear Fluid and the Cornea and Inhibits Epithelial Cell Invasion by *Pseudomonas aeruginosa*, Apr. 2005, Infection and Immunity, vol. 73, No. 4, pp. 2147-2156.*

Akiyama J. et al., "Tissue Distribution of Surfactant Proteins A and D in the Mouse," *J. Histochem. Cytochem.*, 2002, 50, 993-996.

Benton, W.D. et al., "Screening λgt Recombinant Clones by Hybridization to Single Plaques in situ," *Science*, 1977, 196, 180-182.

Bufler, P. et al., "Surfactant Protein A and D Differently Regulate the Immune Response to Nonmucoid Pseudomonas Aeruginosa and Its Lipopolysaccharide," *Am. J. Respir. Cell Mol. Biol.*, 2003, 28(2), 249-256.

Clark E. et al., "Structural Requirements for SP-D Function in vitro and in vivo: Therapeutic Potential of Recombinant SP-D," *Immunobiol.*, 2002, 205(4-5), 619-631.

Crouch, E. et al., "Surfactant Proteins A and D and Pulmonary Host Defense," *Annu. Rev. Physiol.*, 2001, 63, 521-524.

Crouch, E. et al., "Recombinant Pulmonary Surfactant Protein D," *J. Biol. Chem.*, 1994, 269(22), 15808-15813.

Crouch, E., "Collectins and Pulmonary Host Defense," *Am. J. Respir. Cell. Mol. Biol.*, 1998, 19, 177-201.

Geerling, G. et al., "Autologous Serum-Eye-Drops for Ocular Surface Disorders. A Literature Review and Recommendations for Their Application," *Ophthalmologe*, 2002, 99(12), 949-959 (English language abstract included).

Grunstein, M. et al., "Colony Hybridization: A method for the isolation of cloned DNAs that contain a specific gene," *Proc. Natl. Acad. Sci. USA.*, 1975, 72(10), 3961-3965.

Gubler, U. et al., "A simple and very efficient method for generating cDNA libraries,"*Gene*, 1983, 25, 263-269.

Haynes, R.J. et al., "Antimicrobial Defensin Peptides of the Human Ocular Surface," *Br. Ophthalmol*, 1999, 83, 737-741.

Hazlett, L.D. et al., "B7/CD28 Costimulation is Critical in Susceptibility to *Pseudomonas aeruginosa* Corneal Infection: A Comparative Study Using Monoclonal Antibody Blockade and CD28-Deficient Mice," *J. Immunology*, 2001, 166, 1292-1299.

Hickling, T.P. et al., "A recombinant trimeric surfactant protein D carbohydrate recognition domain inhibits respiratory syncytial virus infection in vitro and in vivo," *Eur. J. Immunol.*, 1999, 29(11), 3478-3484.

Keisara, Y. et al., "Surfactant protein D-coated klebsiella pneumoniae stimulates cytokine production in mononuclear phagocytes," *J. Leukoc. Biol.*, 2001, 70(1), 135-141.

(Continued)

*Primary Examiner*—Jon Weber
*Assistant Examiner*—Abdel A Mohamed
(74) *Attorney, Agent, or Firm*—Woodcock Washburn LLP

(57) ABSTRACT

The use of collectins and/or surfactant proteins for the treatment and prevention of ocular disease.

10 Claims, 7 Drawing Sheets

OTHER PUBLICATIONS

Kernacki, K.A. et al., "Macrophage Inflammatory Protein-2 is a Mediator of Polymorphonuclear Neutrophil Influx in Ocular Bacterial Infection," *J. Immunol.*, 2000, 164, 1037-1045.

Kishore et al., "Recent Progress in the Understanding of the Structure-Function Relationships of the Globular Head Regions of C1q," *Immunobiol.*, 2002, 205, 355-364.

Madan, T. et al., "Protective Role of Lung Surfactant Protein D in a Murine Model of Invasive Pulmonary *Aspergillosis,*"*Infect. & Immun.*, 2001, 69(4), 2728-2731.

Madsen, J. et al., "Localization of Lung Surfactant Protein D on Mucosal Surfaces in Human Tissue," *J. Immunol.*, 2000, 164, 5866-5870.

McNamara, N. et al., "Human Tear Components Bind *Pseudomonas aeruginosa,*" *Adv. Exp. Med. Biol.*, 1998, 438, 653-658.

Ofek, I. et al., "Surfactant Protein D Enhances Phagocytosis and Killing of Unencapsulated Phase Variants of *Klebsiella pneumoniae,*" *Infection & Immunol.*, 2001, 69(1), 24-33.

Poon, A. C. et al., "Autologous Serum Eyedrops for Dry Eyes and Epithelial Defects: Clinical and In Vitro Toxicity Studies," *Br. Ophthalmol*, 2001, 85, 1188-1197.

Restrepo, C.I. et al., "Surfactant Protein D Stimulates Phagocytosis of *Pseudomaonas aeruginosa* by Alveolar Macrophages," *Am. J. Respir. Cell Mol. Biol.*, 1999, 21(5), 576-585.

Rudner, X.L. et al., "Prolonged Elevation of IL-1 in *Pseudomonas aeruginosa* Ocular Infection Regulates Macrophage-Inflammatory Protein-2 Production, Polymorphonuclear Neutrophil Persistence, and Corneal Perforation," *J. Immunol.*, 2000, 164, 6576-6582.

Rust, K. et al., "Human Surfactant Protein D: SP-D Contains a C-Type Lectin Carbohydrate Recognition Domain," *Arch. Biochem. Biophys.*, 1991, 290(1), 116-126.

Stahlman, M.T. et al., "Immunolocalization of Surfactant Protein-D (SP-D) in Human Fetal, Newborn, and Adult Tissue," *J. Histochem Cytochem.*, 2002, 50(5), 651-660.

Streilein, J.W., "Immunoregulatory Mechanisms of the Eye," *Progress in Retinal and Eye Research*, 1999, 18(3), 357-370.

Streilin, J.W. et al., "Does Innate Immune Privilege Exist?" *J. Leukoc. Biol.*, 2002, 67(4), 479-487.

White, M.R. et al., "Enhanced Antiviral and Opsonic Activity of a Human Mannose-Binding Lectin and Surfactant Protein D Chimera," *J. Immunol.*, 2000, 165, 2108-2115.

Zhang, L. et al., "Complementation of Pulmonary Abnormalities in SP-D (-/-) Mice with an SP-D/Conglutinin Fusion Protein," *J. Biol. Chem.*, 2002, 277(25), 22453-22459.

\* cited by examiner

| | LDH (Abs 490nm) mean ± SD | |
|---|---|---|
| Cells with bacteria: | | |
| 6206, no tears | 0.49±0.01 | |
| 6206, with tears | 0.14±0.03 | a |
| Controls without bacteria: | | |
| Baseline, no tears | 0.13±0.01 | |
| Baseline, with tears | 0.13±0.01 | |
| 100% cytotoxicity, no tears | 0.78±0.41 | b |
| 100% cytotoxicity, with tears | 0.78±0.13 | |

[a] $p < 0.05$, t-test
[b] 100% cytotoxicity = Triton X-100 treated cells

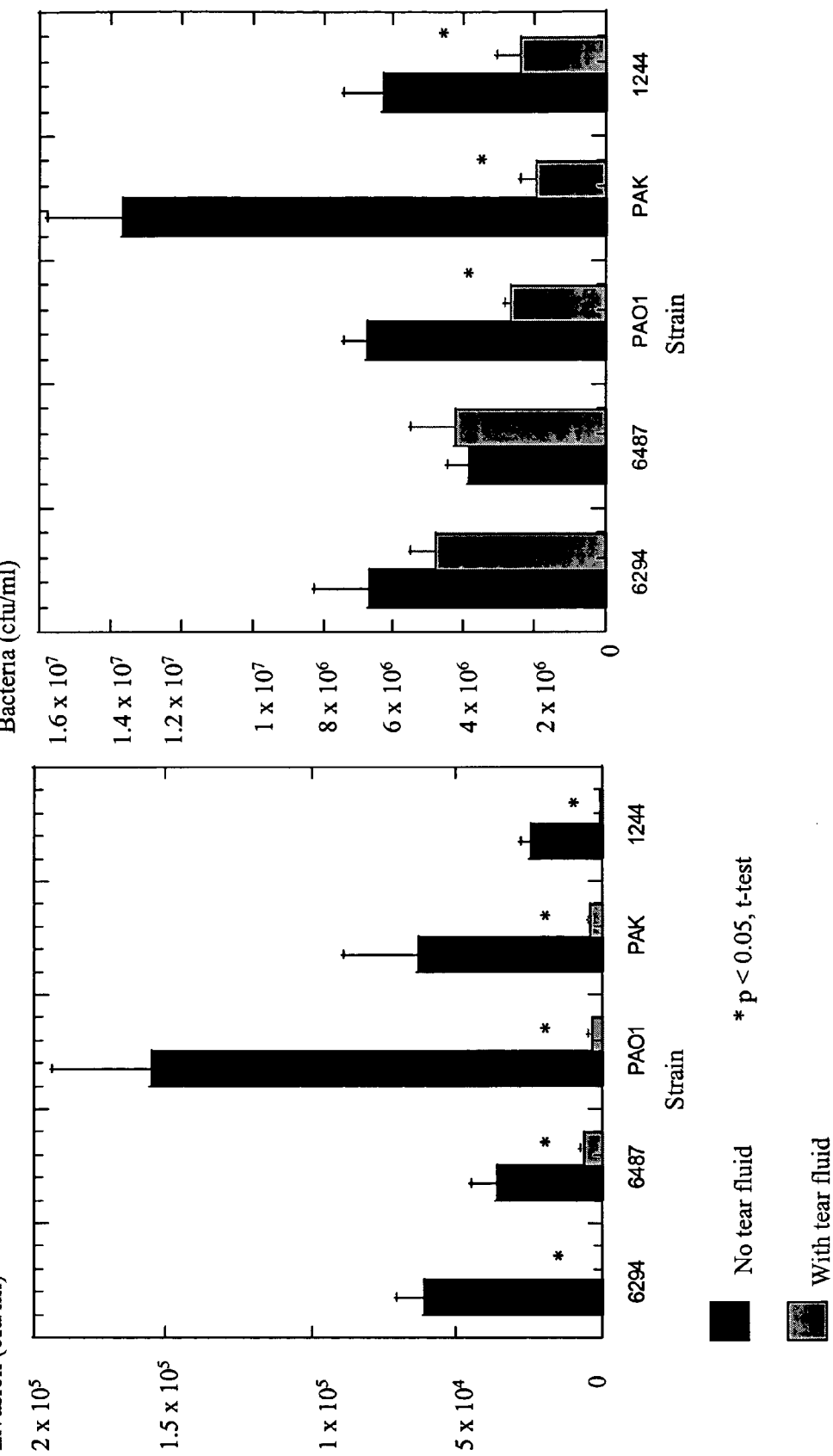

US 7,332,470 B2

METHODS AND COMPOSITIONS FOR TREATING OCULAR DISEASE

CROSS REFERENCE TO RELATED APPLICATIONS

The present application claims priority to U.S. Provisional Application Ser. No. 60/462,913 filed Apr. 15, 2003, which is incorporated herein by reference in its entirety.

U.S. GOVERNMENT RIGHTS

This invention was made with government support under Grant No. EY11221 awarded by the National Institutes of Health. The government has certain rights in the invention.

FIELD

The present invention relates to the use of collectins and/or surfactant proteins for the treatment and prevention of ocular disease.

BACKGROUND

The innate immune system is a mechanism of host defense found in essentially every multicellular organism from plants to humans. It is the primary defense the body has against the multitude of infectious agents that are encountered on a daily basis. The innate response is a non-specific quick response that involves recruiting macrophages and polymorphonuclear granulocytes to sites of infection.

Although the innate immune system provides essential protection against infection by pathogenic agents, its non-specific responses to infectious agents can, in certain situations, have detrimental effects on host tissues (Rudner et al., *The Journal of Immunology*, 2000, 164:6576-6582). In order to protect endogenous tissue from non-specific attacks by components of the innate immune system against such pathogens, certain sites in the body are immune privileged. One such site is the eye. The eye must protect itself against not only invading pathogens but also against the excessive recruitment of macrophages and neutrophils to the eye in a non-specific response mechanism that has the potential to cause great damage to endogenous tissue as a result of inflammation associated with innate immune responses (Streilein, *Progress in Retinal and Eye Research*, 1999, 18:3:357-370). In such instances, therapies are needed that are capable of successfully attacking an invading agent while preserving ocular integrity by blunting a potentially aggressive immune response. The present invention meets this and other needs.

SUMMARY

The present invention provides methods for treating ocular disease in a subject. The methods comprise administering into the eye of a subject one or more collectins. The collectin is present in a sufficient amount to exert a therapeutic effect. In one embodiment, the subject to be treated by the methods of the present invention is a contact lens wearer.

The present invention also provides methods for treating ocular disease in a subject, wherein the pharmaceutical composition to be administered into the eye of the subject comprises a surfactant protein. In one embodiment of the present invention, the surfactant protein is both a collectin and a surfactant protein, i.e., SP-D. The surfactant protein is present in a sufficient amount to exert a therapeutic effect.

Ocular diseases treatable by the methods of the present invention include non-infectious ocular diseases such as dry eye and infectious ocular diseases such as keratitis and conjunctivitis. In certain embodiments of the present invention, the ocular disease is caused by a microbial agent such as a bacterial, viral, fungal, or protozoan pathogen. For example, in one embodiment of the present invention, the microbial agent is a gram-negative bacterium such as *Pseudomonas aeruginosa*.

The present invention also provides ophthalmic compositions comprising a collectin and/or a surfactant protein and a liquid aqueous medium compatible with application to a mammalian eye. In one embodiment of the present invention, the ophthalmic composition is an artificial tear composition. In another embodiment, the ophthalmic composition is for storing, cleaning, re-wetting, or disinfecting a contact lens.

The present invention also provides antimicrobial lenses, i.e., an antimicrobial contact lens, comprising one or more collectins and/or surfactant proteins. In one embodiment, the collectin or surfactant protein is a tear surfactant protein, i.e., SP-D.

The present invention also provides kits for the treatment of a subject having an ocular disease. In one embodiment, the kit comprises a pharmaceutical composition comprising a collectin and instructions for the administration of the collectin. In another embodiment, the kit comprises a pharmaceutical composition comprising a surfactant protein and instructions for the administration of the surfactant protein.

BRIEF DESCRIPTION OF THE DRAWINGS

FIG. 1.

FIG. 2: Bacterial invasion of corneal epithelial cells was quantified using gentamicin survival assays. FIG. 2A demonstrates that whole human tear fluid protects against *P. aeruginosa* invasion of corneal epithelial cells. FIG. 2B demonstrates that tear protection did not require inhibition of bacterial growth.

DETAILED DESCRIPTION

A. General Overview

Figure 1A:
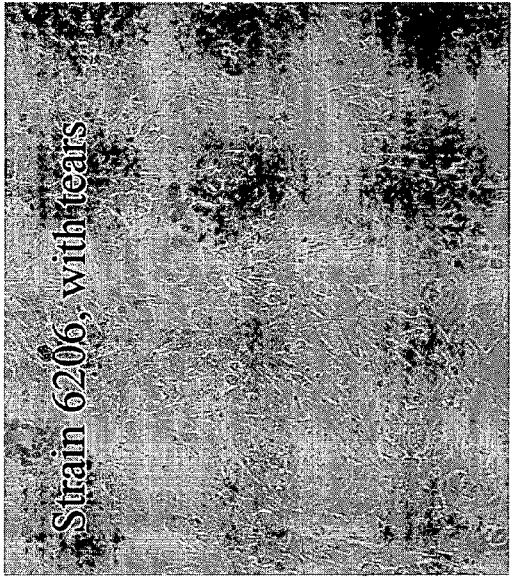
FIG. 1A shows trypan blue staining of corneal cell death after exposure to *Pseudomonas aeruginosa* with or without treatment with tear fluid.

The present invention provides new methods of protecting the eye from ocular disease. The present invention is based, in part, on the surprising discovery that surfactant protein-D is found in large amounts in human tears and protects corneal cells against microbial invasion, e.g., *Pseudomonas aeruginosa* invasion.

Accordingly, the present invention provides methods for treating ocular disease by administering therapeutic compounds, e.g., one or more collectins or surfactant proteins, to a subject. In preferred embodiments, the collectins and/or surfactant proteins are administered as pharmaceutical compositions. The present invention also provides ophthalmic compositions for storing, cleaning, re-wetting, or disinfecting a contact lens as well as antimicrobial lenses.

The term "antimicrobial lens" refers to a lens that (1) inhibits the adhesion of bacteria or other microbes to the lens, (2) inhibits the growth of bacteria or other microbes on the lens, (3) kills bacteria or other microbes on the surface of the lens or in an area surrounding the lens, or (4) inhibits virulence factor expression or function of bacteria or other microbes, i.e., by protecting the eye from microbial invasion. Preferably, the lenses of the invention reduce virulence factor expression or function of bacteria or other microbes by greater than 30%, 50%, 65%, 70%, 75%, 80%, 85%, 90%, more preferably by greater than 91%, 92%, 93%, 94%, 95%, 96%, 97%, 98% or 99%.

As used herein, the term "lens" refers to an ophthalmic device that resides in or on the eye. These devices can provide optical correction or can be cosmetic. The term lens includes, but is not limited to, soft contact lenses, hard contact lenses, intraocular lenses, overlay lenses, ocular inserts, and optical inserts. Soft contact lenses are typically made from silicone elastomers or hydrogels, which include, but are not limited to, silicone hydrogels, and fluorohydrogels.

The term "treating" refers to any indicia of success in the treatment or amelioration or prevention of an ocular disease, including any objective or subjective parameter such as abatement; remission; diminishing of symptoms or making the disease condition more tolerable to the patient; slowing in the rate of degeneration or decline; or making the final point of degeneration less debilitating. The treatment or amelioration of symptoms can be based on objective or subjective parameters; including the results of an eye examination. Accordingly, the term "treating" includes the administration of the compounds or agents of the present invention to prevent or delay, to alleviate, or to arrest or inhibit development of the symptoms or conditions associated with ocular disease. The term "therapeutic effect" refers to the reduction, elimination, or prevention of the disease, symptoms of the disease, or side effects of the disease in the subject.

The term "ocular disease" refers to any disorder of the eye and/or lacrimal system. It includes non-infectious ocular diseases such as non-infectious ocular surface diseases, e.g., dry eye, and infectious ocular disease such as those ocular diseases caused by microbes. Diseases treatable by the methods of the present invention include, but are not limited to, diseases of the eyelid such as infectious and non-infectious blepharitis, hordeolum, preseptal cellulites, chalazion, herpes zoster ophthalmicus, dacryocystitis, herpes simplex blepharitis, orbital cellulites, and entropion; diseases of the conjunctiva and sclera, such as allergic conjunctivitis, vernal keratoconjunctivitis, viral conjunctivitis, bacterial conjunctivitis, episcleritis, scleritis, pingueculitis, ocular cysticercosis, toxic follicular conjunctivitis, and giant papillary conjunctivitis; diseases of the cornea, such as keratitis sicca or dry eye syndrome, herpes simplex keratitis, bacterial keratitis, sterile corneal infiltrates, and Salzmann's nodular degeneration; diseases of the uvea, such as inflammatory glaucoma and uveitis; and diseases of the vitreous and retina. Any ocular disease or condition that would benefit from changes in surface tension in the eye and/or the administration of anti-microbial agents to the eye is treatable by the methods of the present invention. For example, graft vs. host disease (i.e., the rejection of transplanted ocular tissues) can be treated by the present methods. In particular, contact lens associated diseases or conditions are treatable by the methods of the present invention, e.g., bacterial keratitis, contact lens associated red eye ("CLARE"), contact lens induced peripheral ulcers ("CLPU") and infiltrative keratitis ("IK").

The compositions, including lenses, of the present invention possess activity toward microbes, i.e., antimicrobial activity. As used herein, the term "antimicrobial" is meant to include prevention, inhibition, termination, or reduction of virulence factor expression or function of a microbe. "Prevention" can be considered, for example, to be the obstruction or hindrance of any potential microbial growth. "Termination" can be considered, for example, to be actual killing of the microbes by the presence of the composition. "Inhibition" can be considered, for example, to be a reduction in microbial growth or inhibiting virulence factor expression or function of the microbe.

Preferably, the compositions of the present invention will inhibit virulence factor expression or function of a microbe by greater than 30%, 50%, 65%, 70%, 75%, 80%, 85%, 90%, more preferably by greater than 91%, 92%, 93%, 94%, 95%, 96%, 97%, 98% or 99%.

As used herein, "microbe" or "microbial agent" is meant to include any organism comprised of the phylogenetic domains bacteria and archaea, as well as unicellular and filamentous fungi (such as yeasts and molds), unicellular and filamentous algae, unicellular and multicellular parasites, and viruses that causes ocular disease in a subject. Accordingly, such microbial agents include, but are not limited to, bacterial, viral, fungal, or protozoan pathogens.

The methods, lenses, and compositions of the present invention are effective against bacteria including, for example, gram-positive and gram-negative cocci, gram positive and gram negative straight, curved and helical/vibroid and branched rods, sheathed bacteria, sulfur-oxidizing bacteria, sulfur or sulfate-reducing bacteria, spirochetes, actinomycetes and related genera, myxobacteria, mycoplasmas, rickettsias and chlamydias, cyanobacteria, archea, fungi, parasites, viruses and algae. In particular, the present invention is useful against the *Pseudomonas* species of bacteria, e.g., *Pseudomonas aeruginosa*, and other microbes that are found in the eye.

The gram-positive and gram-negative cocci include, but are not limited to, *Aerococcus, Enterococcus, Halococcus, Leuconostoc, Micrococcus, Mobiluncus, Moraxella catarrhalis, Neisseria* (including *N. gonorrheae* and *N. meningitidis*), *Pediococcus, Peptostreptococcus, Staphylococcus* species (including *S. aureus, S. epidermidis, S. faecalis,* and *S. saprophyticus*), *Streptococcus* species (including *S. pyogenes, S. agalactiae, S. bovis, S. pneumoniae, S. mutans, S. sanguis, S. equi, S. equinus, S. thermophilus, S. morbillorum, S. hansenii, S. pleomorphus,* and *S. parvulus*), and *Veillonella*.

The gram-positive and gram-negative straight, curved, helical/vibrioid and branched rods include, but are not limited to, *Acetobacter, Acinetobacter, Actinobacillus equuli, Aeromonas, Agrobacterium, Alcaligenes, Aquaspirillum, Arcanobacterium haemolyticum, Bacillus* species (including *B. cereus* and *B. anthracis*), *Bacteroides* species (including *B. fragilis*), *Bartonella, Bordetella* species (including *B. pertussis*), *Brochothrix, Brucella, Burkholderia cepacia, Calymmatobacterium granulomatis, Campylobacter* species (including *C. jejuni*), *Capnocytophaga, Caulobacter, Chromobacterium violaceum, Citrobacter, Clostridium* species (including *C. perfringens, C. tetani* and *C. difficile*), *Comamonas, Curtobacterium, Edwardsiella, Eikenella, Enterobacter, Erwinia, Erysipelothrix, Escherichia* species (including *E. coli*), *Flavobacterium* species (including *F. meninosepticum*), *Francisella* species (including *F. tularensis*), *Fusobacterium* (including *F. nucleatum*), *Gardnerella* species (including *G. vaginalis*), *Gluconobacter, Haemophilus* species (including *H. influenzae* and *H. ducreyi*), *Hafnia, Helicobacter* (including *H. pylori*), *Herpetosiphon, Klebsiella* species (including *K. pneumoniae*), *Kluyvera, Lactobacillus, Legionella* species (including *L. pneumophila*), *Leptotrichia, Listeria* species (including *L. monocytogenes*), *Microbacterium, Morganella, Nitrobacter, Nitrosomonas, Pasteurella* species (including *P. multocida*), *Pectinatus, Porphyromonas gingivalis, Proteus* species (including *P. mirabilis*), *Providencia, Pseudomonas* species (including *P. aeruginosa, P. mallei, P. pseudomallei* and *P. solanacearum*), *Rahnella, Renibacterium salmoninarum, Salmonella, Serratia, Shigella, Spirillum, Streptobacillus* species (including *S. moniliformis*), *Vibrio* species (including *V. cholerae* and *V vulnificus*), *Wolinella, Xanthobacter, Xenorhabdus, Yersinia* species (including *Y. pestis* and *Y. enterocolitica*), *Zanthomonas* and *Zymomonas*.

The sheathed bacteria include, but are not limited to, *Crenothrix, Leptothrix* and *Sphaerotilus*. The sulfur-oxidizing bacteria include, but are not limited to, *Beggiatoa, Gallionella, Sulfolobus, Thermothrix, Thiobacillus* species (including *T. ferroxidans*), *Thiomicrospira* and *Thiosphaera*. The sulfur or sulfate-reducing bacteria include, but are not limited to, *Desulfobacter, Desulfobulbus, Desulfococcus, Desulfomonas, Desulfosarcina, Desulfotomaculum, Desulfovibrio* and *Desulfuromonas*.

The spirochetes include, but are not limited to, *Treponema* species (including *T. pallidum, T. pertenue, T. hyodysenteriae* and *T. denticola*), *Borrelia* species (including *B. burgdorferi* and *B. recurrentis*), *Leptospira* and *Serpulina*.

The actinomycetes and related genera include, but are not limited to, *Acetobacterium, Actinomyces* species (including *A. israelii*), *Bifidobacterium, Brevibacterium, Corynebacterium* species (including *C. diphtheriae, C. insidiosum, C. michiganese, C. rathayi, C. sepedonicum, C. nebraskense*), *Dermatophilus, Eubacterium, Mycobacterium* species (including *M. tuberculosis* and *M. leprae*), *Nocardia, Propionibacterium, Rhodococcus* and *Streptomyces*.

The myxobacteria include, but are not limited to, *Chondromyces, Cystobacter, Melittangium, Myxococcus, Nannocystis, Polyangium* and *Stigmatella*. The mycoplasmas include, but are not limited to, *Mycoplasma* species (including *M. pneumoniae*), Mycoplasma-like organisms of plants and invertebrates, *Spiroplasma* and *Ureaplasma* species (including *U. urealyticum*).

The rickettsias and chlamydias include, but are not limited to, *Aegyptianella, Anaplasma, Chlamydia* species (including *C. pneumoniae, C. trachomatis* and *C. psittaci*), *Cowdria, Coxiella, Ehrlichia, Eperythrozoon, Haemobartonella, Neorickettsia, Rickettsia* and *Rickettsiella*. The cyanobacteria include, but are not limited to, *Anabaena, Nostoc, Oscillatoria, Pleurocapsa, Prochloron* and *Synechococcus*.

The archea include, but are not limited to, all methanogens (Methanobacterium, *Methanobrevibacter, Methanococcoides, Methanococcus, Methanogenium, Methanolobus, Methanomicrobium, Methanoplanus, Methanosarcina, Methanospirillum, Methanothermus* and *Methanothrix*), and the genera *Acidianus, Archaeoglobus, Desulfurococcus, Haloarcula, Halobacterium, Halococcus, Haloferax, Natronobacterium, Natronococcus, Pyrococcus, Pyrodictium, Staphylothermus, Sulfolobus, Thermococcus, Thermophila, Thermoplasma* and *Thermoproteus*.

The present invention can also be used against fungi which include, but are not limited to, *Acremonium, Aspergillus* species (including *A. flavus, A. niger, A. fumigatus, A. terreus, A. glaucus,* and *A. nidulans*), *Blastomyces* species (including *B. dermatitidis*), *Candida* species (including *C. albicans* and *C. parapsilosis*), *Ceratocystis, Chaetomium, Coccidioides* species (including *C. immitis*), *Cryptococcus* species (including *C. neoformans* and *C. laurenti*) *Epidermophyton, Fusarium* species (including *F. oxysporum* and *F. solani*), *Gongronella, Histoplasma* species (including *H. capsulatum*), *Acremonium, Hormonea, Lasiodiplodia theobromae, Malassezia furfur, Microsporum, Mycosphaerellafijiensis, Paracoccidiodes brasiliensis, Penicillium, Pneumocystis carinii, Pseudallescheria boydii, Pythium, Rhizoctonia, Rhodotorula, Saccharomyces, Sporothrix schenckii, Torula, Trichoderma, Trichophyton* species (including *T. mentagrophytes* and *T. rubrum*) and *Trichothecium*.

The present invention can be used against parasites which include, but are not limited to, *Acanthamoeba* species, *Ascaris lumbricoides, Babesia, Balamuthia, Balantidium, Blastocystis* species including *B. hominis, Chilomastix, Clonorchis sinensis, Cryptosporidium parvum, Cyclospora, Dientamoeba fragilis, Diphyllobothrium, Echinococcus, Endolimax, Entamoeba* species (including *E. histolytica*), *Enterobius* species (including *E. vermicularis*), *Giardia lamblia,* hookworms (including *Necator, Ancylostoma,* and *Unicinaria*), *Hymenolepsis, Iodamoeba, Isospora, Leishmania, Mansonella,* microsporidia, *Microsporidium, Naegleria fowleri, Onchocerca, Plasmodium* (including *P. falciparum, P. vivax, P. ovale* and *P. malariae*), *Schistosoma* (including *S. haematobium* and *S. mansoni*), *Strongyloides* species (including *S. stercoralis*), tapeworms (including *Taenia* species), *Toxoplasma* (including *T. gondii*), *Trichinella* (including *T. spiralis*), *Trichomonas vaginalis, Trichuris* species including *T. trichiura, Trypanosoma, Dirofilaria, Brugia, Wuchereria, Vorticella, Eimeria* species, *Hexamita* species and *Histomonas meleagidis*.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

A particular nucleic acid sequence also implicitly encompasses "splice variants." Similarly, a particular protein encoded by a nucleic acid implicitly encompasses any protein encoded by a splice variant of that nucleic acid. "Splice variants," as the name suggests, are products of alternative splicing of a gene. After transcription, an initial nucleic acid transcript can be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition.

A liquid aqueous medium or other material is ophthalmically acceptable when it is compatible with ocular tissue, that is, it does not cause significant or undue detrimental effects when brought into contact with ocular tissue. An ophthalmic composition or pharmaceutical composition of the present invention is a composition that is compatible with ocular tissue. i.e., a composition that is suitable for administration to the eye.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

"Pharmaceutically acceptable excipient " means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

"Pharmaceutically acceptable salts and esters" means salts and esters that are pharmaceutically acceptable and have the desired pharmacological properties. Such salts include salts that can be formed where acidic protons present in the compounds are capable of reacting with inorganic or organic bases. Suitable inorganic salts include those formed with the alkali metals, e.g. sodium and potassium, magnesium, calcium, and aluminum. Suitable organic salts include those formed with organic bases such as the amine bases, e.g. ethanolamine, diethanolamine, triethanolamine, tromethamine, N methylglucamine, and the like. Such salts also include acid addition salts formed with inorganic acids (e.g. hydrochloric and hydrobromic acids) and organic acids (e.g. acetic acid, citric acid, maleic acid, and the alkane- and arene-sulfonic acids such as methanesulfonic acid and benzenesulfonic acid). Pharmaceutically acceptable esters include esters formed from carboxy, sulfonyloxy, and phosphonoxy groups present in the compounds, e.g. $C_{1-6}$ alkyl esters. When there are two acidic groups present, a pharmaceutically acceptable salt or ester can be a mono-acid-mono-salt or ester or a di-salt or ester; and similarly where there are more than two acidic groups present, some or all of such groups can be salified or esterified. Compounds named in this invention can be present in unsalified or unesterified form, or in salified and/or esterified form, and the naming of such compounds is intended to include both the original (unsalified and unesterified) compound and its pharmaceutically acceptable salts and esters. Also, certain compounds named in this invention may be present in more than one stereoisomeric form, and the naming of such compounds is intended to include all single stereoisomers and all mixtures (whether racemic or otherwise) of such stereoisomers.

The terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects to a degree that would prohibit administration of the composition.

A "therapeutically effective amount" means the amount that, when administered to a subject for treating a disease, is sufficient to effect treatment for that disease.

Except when noted, the terms "subject" or "patient" are used interchangeably and refer to mammals such as human patients and non-human primates, as well as experimental animals such as rabbits, dogs, cats, rats, mice, and other animals. Accordingly, the term "subject" or "patient" as used herein means any mammalian patient or subject to which the compositions of the invention can be administered. In some embodiments of the present invention, the patient will be suffering from a condition that causes lowered resistance to disease, e.g., HIV. In an exemplary embodiment of the present invention, to identify subject patients for treatment with a pharmaceutical composition comprising one or more collectins and/or surfactant proteins according to the methods of the invention, accepted screening methods are employed to determine the status of an existing disease or condition in a subject or risk factors associated with a targeted or suspected disease or condition. These screening methods include, for example, ocular examinations to determine whether a subject is suffering from an ocular disease. These and other routine methods allow the clinician to select subjects in need of therapy. In certain embodiments of the present invention, ophthalmic compositions for storing, cleaning, re-wetting and/or disinfecting a contact lens, as well as artificial tear compositions and/or contact lenses will contain one or more collectins and/or surfactant proteins thereby inhibiting the development of ocular disease in contact-lens wearers.

"Treating" or "treatment" of an ocular infection using the methods of the present invention includes preventing the onset of symptoms in a subject that may be at increased risk of ocular infection but does not yet experience or exhibit symptoms of infection, inhibiting the symptoms of infection (slowing or arresting its development), providing relief from the symptoms or side-effects of infection (including palliative treatment), and relieving the symptoms of infection (causing regression).

"Concomitant administration" of a known antimicrobial drug with a pharmaceutical composition of the present invention means administration of the drug and the collectin and/or surfactant protein composition at such time that both the known drug and the composition of the present invention will have a therapeutic effect. Such concomitant administration may involve concurrent (i.e., at the same time), prior, or subsequent administration of the antimicrobial drug with respect to the administration of a compound of the present invention. A person of ordinary skill in the art, would have no difficulty determining the appropriate timing, sequence and dosages of administration for particular drugs and compositions of the present invention.

B. Therapeutic Agents

The collectins comprise a family of innate immune molecules characterized by the presence of a collagen-like domain and a calcium-dependent lectin domain, commonly referred to as a carbohydrate recognition domain (Crouch, *Am. J. Respir. Cell. Mole. Biol.*, 1998, 19:177-201). The known collectins include surfactant protein-A, surfactant protein-D, CL-43, serum mannan-binding protein (MBP) also referred to as serum mannan-binding lectin (MBL), and conglutinin. Collectins have been shown to have specific interactions with various microorganisms and have been demonstrated to modulate local inflammatory and immune responses in the lung. One member of the collectin family in particular, SP-D, has been shown to interact with a wide variety of respiratory pathogens, modulate the leukocyte response to these organisms, and participate in aspects of pulmonary immune and inflammatory regulation. (Crouch, supra; Crouch and Wright, *Annu. Rev. Physiol.* 2001: 63:521-524). For example, SP-D has been shown to stimulate the migration of human neutrophils, monocytes, and macrophages in response to respiratory infection, promote phagocytosis in the lung (Madsen et al. *The Journal of Immunology,* 2000, 164:5866-5870), and enhance the internalization and killing of certain mucoid strains of *Pseudomonas aeruginosa* in the lung (Restrepo et al., *Am. J. Respir. Cell Mol. Biol.* 1999, 21(5):576-585). SP-D has also been demonstrated to be a potent chemoattractant and haptotactic agent for both monocytes and neutrophils.

The collectins can be divided into families based on their quaternary structure. (Hartshorn et al., *The Journal of Immunology*, 2000, 165:2108-2115) Typically, collectins exist in oligomeric form comprising trimeric subunits. Each subunit consists of four major domains: a short cysteine-containing $NH_2$ terminal cross-linking domain; a triple helical collagen domain of variable length; a trimeric coiled-coil linking domain; and a carboxyl terminal, C-type lectin carbohydrate recognition domain (Crouch, supra).

Collectins are expressed in various sites throughout the body. Although originally identified as an essential part of both the physiological and immune defense functions of the airways, it has recently become apparent that collectins are present at other sites in the human body and can form an important part of the mucosal immune defenses. SP-D, for example, has been detected in human epithelial cells and luminal material in lacrimal glands, salivary glands, pancreas, bile ducts, renal tubules, esophageal muscle and glands, parietal cells of the stomach, crypts of Lieberkuhn, sebaceous and eccrine sweat glands, Von Ebner's glands, endocervical glands, seminal vesicles, adrenal cortex, myocardium, and the anterior pituitary gland. (Stahlman et al., *J. Histochem Cytochem.,* 2002, 50: 651-660, Akiyama et al. *J. Histochem. Cytochem.,* 2002, 50: 993-996 ). SP-D is synthesized at particularly high concentrations by Type II epithelial cells and nonciliated bronchiolar epithelial cells in the lung. SP-A has been found in the lung, trachea, and esophagus, as well as the liver, stomach, jejunum, pancreas, spleen, heart, testes and ovaries of mice. (Akiyama et al., supra). The present inventors are the first to find collecting, e.g., SP-D, present in large amounts in human tears.

Collectins that can be used in the present invention are typically mammalian collecting. For example, they can be from primates, e.g., human; rodents, e.g., rat, mouse, hamster; cows, pigs, horse, sheep, or any mammal. The collectins of the invention include both naturally occurring or non-naturally occurring collecting, e.g., truncated collectins retaining antimicrobial activity, conservatively modified variants of collectins retaining antimicrobial activity, and recombinant collecting, including collectin fusion proteins. For examples of recombinant forms of SP-D and SP-D fusion proteins for use in the present invention, see Hickling et al., *Eur. J. Immunol.*, 1999, 29(11):3478-3484; Zhang et al. *J. Biol. Chem.*, 2002, 277(25):22453-22459; Madan et al, *Infect. Immun.*, 2001, 69(4):2728-2731; White et al., *The Journal of Immunology*, 2000, 165:2108-2115, Kishore et al., *Immunobiol.*, 2002, 205:355-364; Crouch et al., *J. Biol.Chem.* 269(22):15808-15813, Clark et al., *Immunobiol.*, 2002, 205(4-5): 619-631, and U.S. Pat. No. 6,110,708, each of which is incorporated by reference herein in its entirety and for all purposes. A collectin of the present invention typically has anti-microbial activity. Anti-microbial assays can be performed according to methods known to those of skill in the art. For example, samples or assays comprising microbial agents that are treated with a composition of the present invention can be compared to control samples comprising microbial agents that are not treated with a composition of the present invention to examine the extent of reduction of microbial virulence factor expression or function in the sample or assay. Control samples are assigned a relative virulence factor expression or function of 100%. Inhibition of microbial activity is achieved when the virulence factor expression or function relative to the control is reduced, e.g., about 80% or less, preferably 50%, more preferably 25-0%.

Collectins and/or surfactant proteins, or functional fragments thereof, can be produced by routine means using readily available starting materials. The nucleic acid sequences encoding collectins as well as the amino acid sequences of the proteins are well known. Sequence information for collectin proteins and nucleic acids can be found in GenBank. By way of non-limiting examples, collectin protein sequences include those of conglutinin (accession number NP_783630, I45878, BAA03170, CAA50665, AAA20126), surfactant protein D (accession number NP_037010, CAA46152, AAB25037 (collagenous region), AAB25038 (noncollagenous region), AAF15277, NP_003010, S33603, CAA53510, CAB40823, CAB40825), surfactant protein A (AAA85516, AAA31468, 2202163A, 1901176A, AAB61294, AAF02223, BAA97976, AAF28384, AAF18995, AAB82952), collectin 43 (A53570, CAA53511), and MBP (BAB 17020), each of which is incorporated herein by reference in its entirety. Collectin nucleic acid sequences include accession numbers X65018, L10123, and D14085, each of which is incorporated herein by reference in its entirety. The nucleic acid sequences encoding surfactant proteins as well as the amino acid sequences of the proteins are also well known in the art. Sequence information for surfactant proteins and nucleic acids encoding surfactant proteins can be found in GenBank. By way of non-limiting examples, surfactant protein sequences include those of SP-D (accession number NP_037010, CAA46152, AAB25037 (collagenous region), AAB25038 (noncollagenous region), AAF15277, NP_003010, S33603, CAA53510, CAB40823, CAB40825), SP-A (AAA85516, AAA31468, 2202163A, (NP_620197, I46531, A29667, NP_680088, P15782, CAB96174), and SP-C (AAB60332, LNBOC1, G02964, WP_059038). Nucleic acid sequences encoding surfactant proteins include accession numbers UO2948 and L11573, each of which is incorporated herein by reference in its entirety.

There are a variety of publications relating to sequence information for the different collectins and/or surfactant proteins, citations of which are linked to the sequence information in GenBank. Each of these references (for example, Rust et al. *Arch. Biochem. Biophys.*, 1991, 290 (1):116-126) including the publicly available sequence information, is incorporated herein by reference in its entirety. The known natural collectins and surfactant proteins are described in the present application. It will be appreciated that additional natural collectins and/or surfactant proteins useful in the methods of the present invention can be identified in the future from either the species set forth herein or other species.

For the methods described herein, naturally occurring, chemically synthesized, commercially available, and recombinantly produced collectins and/or surfactant proteins can be used. Accordingly, this invention relies, in part, on routine techniques in the field of recombinant genetics and molecular biology. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and Ausubel et al., supra)

Collectin and/or surfactant protein nucleic acids, polymorphic variants, orthologs, and alleles can be isolated using nucleic acid probes and oligonucleotides under stringent hybridization conditions, by screening libraries. Alternatively, expression libraries can be used to clone protein, pre-proprotein, polymorphic variants, orthologs, and alleles of the present invention by detecting expressed homologs immunologically with antisera or purified antibodies made against human collectin, surfactant protein D, or portions thereof. Alternatively, tissue culture techniques can also be used to produce collectins, for example, corneal epithelial cells produce SP-D when grown in culture in vitro.

Naturally occurring collectins and/or surfactant proteins can be purified from any collectin or surfactant protein source, e.g., from alveolar type II cells or epithelial tissue, as well as from collectin-expressing or surfactant protein-expressing cells or tissue of other mammals, such as mouse and cow. To make a cDNA library, one should choose a source that is rich in collectin and/or surfactant protein RNA. The mRNA can be made into cDNA using reverse transcriptase, ligated into a recombinant vector, and transfected into a recombinant host for propagation, screening and cloning. Methods for making and screening cDNA libraries are well known (see, e.g., Gubler & Hoffman, *Gene*, 1983, 25:263-269; Sambrook et al., supra; Ausubel et al., supra).

For a genomic library, the DNA can be extracted from the tissue and either mechanically sheared or enzymatically digested to yield fragments of about 12-20 kb. The fragments can then be separated by gradient centrifugation from undesired sizes and are constructed in bacteriophage lambda vectors. These vectors and phage can be packaged in vitro. Recombinant phage can be analyzed by plaque hybridization as described in Benton & Davis, *Science*, 1977, 196:180-182. Colony hybridization is carried out as generally described in Grunstein et al., *Proc. Natl. Acad. Sci. USA.*, 1975, 72:3961-3965.

An alternative method of isolating nucleic acids and orthologs, alleles, mutants, polymorphic variants, and conservatively modified variants of the present invention combines the use of synthetic oligonucleotide primers and amplification of an RNA or DNA template (see U.S. Pat Nos. 4,683,195 and 4,683,202; PCR Protocols: A Guide to Methods and Applications (Innis et al., supra). Methods such as polymerase chain reaction (PCR) and ligase chain reaction (LCR) can be used to amplify nucleic acid sequences of human collectin and/or surfactant protein directly from mRNA, from cDNA, from genomic libraries or cDNA libraries. Degenerate oligonucleotides can be designed to amplify collectin or surfactant protein homologs using the sequences provided herein. Restriction endonuclease sites can be incorporated into the primers. Polymerase chain reaction or other in vitro amplification methods can also be useful, for example, to clone nucleic acid sequences that code for proteins to be expressed, to make nucleic acids to use as probes for detecting the presence of collectin encoding or surfactant protein encoding mRNA in physiological samples, for nucleic acid sequencing, or for other purposes. Genes amplified by the PCR reaction can be purified from agarose gels and cloned into an appropriate vector.

Gene expression of collectins or surfactant proteins can also be analyzed by techniques known in the art, e.g., reverse transcription and amplification of mRNA, isolation of total RNA or poly $A^+$RNA, northern blotting, dot blotting, in situ hybridization, RNase protection, high density polynucleotide array technology, e.g., and the like.

The gene for a collectin or surfactant protein is typically cloned into intermediate vectors before transformation into prokaryotic or eukaryotic cells for replication and/or expression. These intermediate vectors are typically prokaryote vectors, e.g., plasmids, or shuttle vectors.

Provision of a suitable DNA sequence encoding a desired protein permits the production of the protein using recombinant techniques now known in the art. One having ordinary skill in the art can, using well known techniques, can obtain a DNA molecule encoding a protein of the present invention and insert that DNA molecule into a commercially available expression vector for use in well known expression systems. One having ordinary skill in the art can use these commercial expression vectors systems or others to produce collectin proteins or surfactant proteins using routine techniques.

One having ordinary skill in the art can use other commercially available expression vectors and systems or produce vectors using well known methods and readily available starting materials. Expression systems containing the requisite control sequences, such as promoters and polyadenylation signals, and preferably enhancers, are readily available and known in the art for a variety of hosts. See, e.g., Ausubel et al., supra. Thus, the desired proteins can be prepared in both prokaryotic and eukaryotic systems, resulting in a spectrum of processed forms of the protein.

The most commonly used prokaryotic system remains *E. coli*, although other systems such as *Bacillus subtilis* and *Pseudomonas* are also useful. Suitable control sequences for prokaryotic systems include both constitutive and inducible promoters including, but not limited to, the lac promoter, the trp promoter, hybrid promoters such as the tac promoter, the lambda phage Pl promoter. In general, foreign proteins can be produced in these hosts either as fusion or mature proteins. When the desired sequences are produced as mature proteins, the sequence produced can be preceded by a methionine which is not necessarily efficiently removed. Accordingly, the peptides and proteins claimed herein can be preceded by an N terminal Met when produced in bacteria. Moreover, constructs can be made wherein the coding sequence for the peptide is preceded by an operable signal peptide which results in the secretion of the protein. When produced in prokaryotic hosts in this matter, the signal sequence is removed upon secretion.

A wide variety of eukaryotic hosts are also now available for production of recombinant foreign proteins. As in bacteria, eukaryotic hosts can be transformed with expression systems which produce the desired protein directly, but more commonly signal sequences are provided to effect the secretion of the protein. Eukaryotic systems have the additional advantage that they are able to process introns which can occur in the genomic sequences encoding proteins of higher organisms. Eukaryotic systems also provide a variety of processing mechanisms which result in, for example, glycosylation, carboxy terminal amidation, oxidation or derivatization of certain amino acid residues, conformational control, and so forth.

Commonly used eukaryotic systems include, but are not limited to, yeast cells, fungal cells, insect cells, mammalian cells, avian cells, and cells of higher plants. Suitable promoters are available which are compatible and operable for use in each of these host cell types. Also available, are termination sequences and enhancers, such as, for example, the baculovirus polyhedron promoter. As described above, promoters can be either constitutive or inducible. For example, in mammalian systems, the mouse metallothionine promoter can be induced by the addition of heavy metal ions. The particulars for the construction of expression systems suitable for desired hosts are known to those in the art. The recombinant proteins can subsequently be separated from host proteins by standard separation techniques known to those of skill in the art.

Standard protein separation techniques for purifying recombinantly produced proteins include solubility fractionation, size differential filtration, and column chromatography.

Often as an initial step, and if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol is to add saturated ammonium sulfate to a protein solution so that the resultant ammonium sulfate concentration is between 20-30%. This will precipitate the most hydrophobic proteins. The precipitate is discarded (unless the protein of interest is hydrophobic) and ammonium sulfate is added to the supernatant to a concentration known to precipitate the protein of interest. The precipitate is then solubilized in buffer and the excess salt removed if necessary, through either dialysis or diafiltration. Other methods that rely on solubility of proteins, such as cold ethanol precipitation, are well known to those of skill in the art and can be used to fractionate complex protein mixtures.

Based on a calculated molecular weight, a protein of greater and lesser size can be isolated using ultrafiltration through membranes of different pore sizes (for example, Amicon or Millipore membranes). As a first step, the protein mixture is ultrafiltered through a membrane with a pore size that has a lower molecular weight cut-off than the molecular weight of the protein of interest. The retentate of the ultrafiltration can then be ultrafiltered against a membrane with a molecular cut off greater than the molecular weight of the protein of interest. The recombinant protein will pass through the membrane into the filtrate. The filtrate can then be chromatographed as described below.

The proteins of interest can also be separated from other proteins on the basis of their size, net surface charge, hydrophobicity and affinity for ligands. In addition, antibodies raised against proteins can be conjugated to column matrices and the proteins immunopurified. All of these methods are well known in the art.

Immunoaffinity chromatography using antibodies raised to a variety of affinity tags such as hemagglutinin (HA), FLAG, Xpress, Myc, hexahistidine (His), glutathione S transferase (GST) and the like can be used to purify polypeptides. The His tag will also act as a chelating agent for certain metals (e.g., Ni) and thus the metals can also be used to purify His-containing polypeptides. After purification, the tag is optionally removed by specific proteolytic cleavage.

It will be apparent to one of skill that chromatographic techniques can be performed at any scale and using equipment from many different manufacturers (e.g., Pharmacia Biotech).

The collectins or surfactant proteins of the present invention can be obtained from commercial sources. For example, commercial preparations of SP-B and SP-C from bovine lungs are sold by Abbot Laboratories as SURVANTA® (beractant) or by Boehringer Ingelheim as ALVEOFACT® (bovactant). Commercial preparations of SP-B and SP-C from calf lungs are sold by Forrest Laboratories as INFA-SURF® (calfactant) and commercial preparations of SP-B and SP-C from porcine lungs are sold by Dey Laboratories as CUROSURF® (poractant-alfa).

C. Pharmaceutical Compositions and Administration

The present invention provides methods of administering a collectin and/or surfactant protein to the eye to treat ocular disease. Thus, exemplary compositions according to the present invention are suitable for direct administration to a subject's eye. By "direct administration" it is meant that the compositions are applied topically or by injection or installation into the eye. There are a wide variety of suitable formulations of pharmaceutical compositions of the present invention (See e.g., Remington's Pharmaceutical Sciences, 19th ed., 1995).

The compositions of the present invention can be compounded with one or more agents to facilitate their use in a wide variety of contexts. Topical compositions for delivering collectins and or surfactant proteins to the eye according to the present invention will typically comprise the collectin and/or surfactant protein present in a suitable ophthalmically acceptable carrier. Exemplary ophthalmically acceptable carriers include, but are not limited to, water, buffered aqueous solutions, isotonic mixtures of water and water-immiscible solvents, such as alkanols, aryl alkanols, vegetable oils, polyalkalene glycols, petroleum-based jellies, ethylcellulose, ethyloleate, carboxymethylcelluloses, polyvinylpyrrolidones, and isopropyl myristates. The compositions of the present invention can also include ophthalmically acceptable auxiliary components such as buffers, emulsifiers, preservatives, wetting agents, tonicity agents, thixotropic agents, e.g., polyethylene glycols, chelating agents, and additional antimicrobial agents. The compositions of the present invention are formulated as sterile, substantially isotonic, and are in full compliance with all Good Manufacturing Practice (GMP) regulations of the U.S. Food and Drug Adminstration.

In exemplary embodiments of the present invention, ophthalmically acceptable compositions of the present invention comprising one or more collectins and/or surfactant proteins can be aqueous suspensions containing a buffer, (e.g., carbonate salt, phosphate salt, acetate salt, glutamic acid, or citrate salt), an isotonizing agent (e.g., glycerol, mannitol, sorbitol, propylene glycol, sodium chloride, potassium chloride, boric acid), a stabilizer (e.g., sodium edetate, sodium citrate), a non-protein based surfactant (e.g., polysorbate 80, polyoxyethylene(60) hydrogenated castor oil, tyloxapol, benzalkonium chloride, polyoxyethylene fatty acid esters, polyoxyethylene alkylphenyl ethers, and polyoxyethylene alkyl ethers, mixtures thereof), a preservative (e.g., p-hydroxybenzoate and its analogs, benzalkonium chloride, benzethonium chloride, chlorobutanol), a pH control agent (e.g., hydrochloric acid, sodium hydroxide, phosphoric acid), a surfactant polyoxyethylene fatty acid esters, and/or other additives. In some embodiments, the ophthalmically acceptable compositions will further comprise a delivery-enhancing transporter to facilitate delivery of the active agent across the ocular tissue (see U.S. Publication No. 20030022831, incorporated by reference in its entirety and for all purposes).

The therapeutic agents of the present invention, i.e., collectins or surfactant proteins, can be incorporated into suitable ophthalmically acceptable carriers at therapeutically effective concentrations. For treatment purposes, the pharmaceutical formulations of the present invention can be, for example, administered to the subject in a single bolus delivery, via continuous delivery over an extended time period, or in a repeated administration protocol (e.g., by an hourly, daily or weekly, repeated administration protocol). The pharmaceutical formulations of the present invention can be administered, for example, one or more times half-hourly, i.e., every half an hour for a 24 hour period, one or more times hourly, or one or more times daily. In certain embodiments, the pharmaceutical formulations of the invention are administered two times daily, four times daily, six times daily, or twelve times daily. Typically, the formulations are self-administered.

In preferred embodiments, a therapeutically effective dosage of one or more collectins and/or surfactant proteins will yield clinically significant results to alleviate one or more symptoms or detectable conditions associated with ocular infection. Determination of effective dosages is typically based on animal model studies followed up by human clinical trials and is guided by determining effective dosages and administration protocols that significantly reduce the occurrence or severity of targeted exposure symptoms or conditions in the subject. Suitable models in this regard include, for example, murine, rat, porcine, feline, non-human primate, and other accepted animal model subjects known in the art. Alternatively, effective dosages can be determined using in vitro models (e.g., immunologic and histopathologic assays). Using such models, only ordinary calculations and adjustments are typically required to determine an appropriate concentration and dose to administer a therapeutically effective amount of the biologically active agent (e.g., amounts that are effective to elicit a desired response). In alternative embodiments, an "effective amount" or "effective dose" of the biologically active agent (s) can simply inhibit or enhance one or more selected biological activity(ies) correlated with ocular infections for either therapeutic or diagnostic purposes.

The actual dosage of biologically active agents will of course vary according to factors such as the extent of exposure and particular status of the subject (e.g., the subject's age, size, fitness, extent of symptoms, susceptibility factors, etc), time and route of administration, as well as other drugs or treatments being administered concurrently.

Dosage regimens can be adjusted to provide an optimum prophylactic or therapeutic response. By "therapeutically effective dose" herein is meant a dose that produces effects for which it is administered. The exact dose will be ascertainable by one skilled in the art using known techniques (see, e.g., Lieberman, Pharmaceutical Dosage Forms (Vols. 1-3, 1992); Lloyd, The Art, Science, and Technology of Pharmaceutical Compounding (1999); and Pickar, Dosage Calculations (1999)). A therapeutically effective dose is also one in which any toxic or detrimental side effects of the biologically active agent is outweighed in clinical terms by therapeutically beneficial effects.

The compositions of the present invention are preferably administered topically or by intraocular injection (e.g., intravitreal, subconjunctival, retrobulbar injection). Topical administration includes the application of the compositions of the present invention to the cul-de-sac of the eye from a dropper controlled bottle or dispenser. In an exemplary embodiment, such compositions can have a concentration in the range from, for example, about 1 µg to about 1 g collectin or surfactant protein per mL of fluid, preferably from about 10 µg to about 5 mg collectin or surfactant protein per mL of fluid, more preferably from about 100 µg to about 1 mg collectin or surfactant protein per mL of fluid, with the particular concentration depending on which collectin or surfactant protein is being employed. In the case of SP-D, SP-D can be present in concentrations from, for example, about 100 µg to about 5 mg per mL of fluid. For each particular subject, specific dosage regimens should be evaluated and adjusted over time according to the individual need and professional judgment of the person administering or supervising the administration of the pharmaceutical compositions. In some embodiments of the present invention, the drops will be administered by "bunching", e.g., multiple doses administered over a 5 minute period, repeated 4 times daily.

Topical administration according to the present invention also includes the application of ophthalmic ointments and gels containing one or more collectins and/or surfactant proteins to the eye. The ophthalmic ointments can include any substances known to the skilled formulation chemist to be useful for the preparation of such ointments. Typically, the ophthalmic ointments will include a base which permits diffusion of the drug into the ocular fluid. In exemplary embodiments of the present invention, the base will be comprised of white petrolatum and mineral oil and other substances known in the art as being appropriate for administration to the eye, e.g., anhydrous lanolin and/or polyethylene-mineral oil gel. The amount of a collectin or surfactant protein in the ointment or gel can vary widely depending on the type of composition, size of a unit dosage, kind of excipients, and other factors well known to those of ordinary skill in the art. Preferably, the final composition will comprise from, for example, 0.000001 percent by weight (wt %) to about 10 wt % of the collectin or surfactant protein, preferably 0.00001 wt % to 1 wt %, with the remainder being the excipient or excipients.

The collectin or surfactant protein containing eye drops used in the present invention can include any agents known to the skilled formulation chemist to be useful for eye drop preparations. For example, in certain embodiments of the present invention, the eye drops can contain an isotonic agent added to sterilized purified water, a preservative, a buffering agent, a stabilizer, a viscous vehicle, and/or an additional antimicrobial agent. In such embodiments of the present invention, the isotonic agents include, but are not limited to sodium chloride, glycerin, or mannitol; the preservatives include, but are not limited to, p-hydroxybenzoic acid ester, or benzalkonium chloride; the buffering agents include, but are not limited to, sodium hydrogenphosphate, sodium dihydrogenphosphate, or boric acid; the stabilizing agents include, but are not limited to sodium edetate; the viscous vehicle includes, but is not limited to, polyvinyl alcohol, polyvinyl pyrrolidone, or polyacrylic; and the pH controller includes, but is not limited to, sodium hydroxide, or hydrochloric acid. A suitable pH range for use as an ophthalmic medicine is preferably within the range of 5 to 9, more preferably between about 7 and 8.5, and most preferably between about 7.2 to about 7.5.

Controlled-release formulations and articles, where the total amount of collectin or surfactant protein is released over time, e.g., over a number of minutes or hours are suitable for the present invention. Typically, the total dosage of the collectin or surfactant protein will be within the limits described above for non-controlled-release formulations, but some cases can be greater, particularly when the controlled-release formulations act over relatively long periods of time. Suitable controlled-release articles for use with the compositions of the present invention include solid ocular inserts. Such inserts are well-known to the skilled formulation chemist available and can be obtained, for example, from commercial vendors such as Alza Corporation, Palo Alto, Calif., and from Oculex Corporation, Palo Alto, Calif.

Using the methods of the present invention, one or more collectins or surfactant proteins can be administered in combination with other known therapies to treat a subject suffering from an ocular disease. In some instances, drugs currently used to treat a eye disease will be effective at lower dosages than would be possible in the absence of a collectin and/or surfactant protein. The precise dosage of a therapeutic agent to be delivered to a subject concomitantly with a collectin or surfactant protein will be dependent upon the discretion and professional judgment of an attendant physician and will be, in part, dependent on such factors as the age, weight and particular disease of the subject. The amount and precise regime will also depend on other factors including the severity of the ocular disease to be treated. Drugs currently used to treat eye diseases of the present invention include antiviral agents, including, but not limited to, trifluridine, valacyclovir, cidofovir, ritonavir, indinavir, AZT, and other anti-HIV agents; antibacterial agents (e.g., antibiotics) including, but not limited to, Antipseudomonal penicillins, (e.g. carbenicillin, ticarcillin, piperacillin) Fluoroquinolones, (e.g. ciprofloxacin, levofloxacin, ofloxacin), azithromycin, clarithromycin, vancomycin, trimethoprim, sulfamethoxazole, and methicillin; antifungal agents including, but not limited to, Natamycin; corticosteroids, including, but not limited to, Fluorometholone, Rimexolone, and Lotepredonol; antiprotozoals, including, but not limited to, Metronidazole; antiparasitic drugs, including, but not limited to, Albendazole, praziquantel, and niclosamide; anti-inflammatory agents and/or any agent used to treat dry eye (e.g., lubricants). Additional examples of drugs appropriate for use with the present invention include, but are not limited to, gentamicin, erythromycin, neomycin, polymyxin B and bacitracin, tobramycin, dexamethasone, hydrocortisone, sulfacetamide, prednisolone acetate (Blephamide), prednisolone sodium phosphate (Vasocidin), tetracycline, dicloxacillin, amoxicillin, nafacillin, oxacillin or cefazolin, ampicillin, clindamycin, triamcinolone acetonide, acyclovir, scopolamine, are amphotericin B, flucytosine, fluconazole, itraconazole, ceftriaxone, pyrimethamine, sulfadiazine, clindamycin, doxycycline, ganciclovir foscarnet, and the like.

A topical solution in accordance with one embodiment of the present invention comprises incorporating a therapeutic dose of one or more collectins or surfactant proteins in an artificial tear formulation. Typically, artificial tear compositions contain ionic components found in normal human tear film, as well as various combinations of one or more of tonicity agents, buffers, viscosity/lubricating agents, non-ionic surfactants, sequestering agents, and preservatives. In certain embodiments of the present invention, the artificial tear compositions will be administered to a subject not yet suffering from an ocular disease for preventative purposes.

Topical administration according to the present invention also includes the incorporation of collectins or surfactant proteins in compositions for storing, cleaning, rinsing, disinfecting, conditioning or rewetting of a contact lens. Accordingly, the present invention can be used in a wide variety of single-purpose and multipurpose ophthalmic solutions, as well as in those solutions not intended for contact lens. Such compositions can also include, but are not limited to, non-protein based surfactants/detergents, chelator cations, osmotic stabilizers, bacteriostatic adjuvants, demulcents, viscosity-adjusting agents, and lubricants. In most preferred embodiments, the added reagents are selected for compatibility with administration to a mammalian eye.

The quantities and relative proportions of each of the ophthalmically acceptable components incorporated into an ophthalmic composition comprising one or more collectins or surfactant proteins are readily determinable by the skilled formulation chemist. Representative components suitable for incorporation into an ophthalmic composition are set forth below.

Buffers for use in ophthalmic compositions for storing, cleaning, rinsing, disinfecting, conditioning or rewetting of a contact lens include a variety of conventional buffers. The choice of the particular buffer system depends on the particular applications intended for the ophthalmic solution. Methods of preparing such buffers are well known in the art and can be found, for example, in a number of standard laboratory manuals (see e.g., Sambrook et al,supra). The buffer is also selected to provide a pH which is compatible with the eye and if the solution is intended for use with a contact lens, with any contact lenses with which it is intended for use. Ideally, the pH of the buffer and hence the pH of the ophthalmic solution is neutral to slightly alkaline. Generally, it is preferred that the ophthalmic solution have a pH between about 5 to 9, more preferably between about 7 and 8.5, and most preferably between about 7.2 to about 7.5. Representative buffers include, but are not limited to, phosphate, borate, citrate, acetate, bicarbonate, histidine, tris, and bis-tris. Exemplary buffers include phosphate buffers, e.g., sodium phosphate buffers, and alkali metal borates such as sodium or potassium borates. The buffer is generally present in a concentration no greater than about 100 mM, and preferably ranges in concentration from about 0.1 to about 5 mM, more preferably from about 0.5 to about 15 mM, and most preferably from about 1-10 mM.

The ophthalmic solutions of the present invention can be adjusted with tonicity agents, to approximate the osmotic pressure of normal tear fluid, which is equivalent to about 0.9 wt %. Concentrations ranging from about 0.001 to about 2.5 wt %, more preferably from about 0.5 to about 1.0 wt %, and most preferably from about 0.8 to about 0.9 wt % are preferred. Tonicity adjusting agents are well known to those of skill in the art and include, but are not limited to, mannitol, sorbitol, dextrose, sucrose, urea, glycerin, propylene glycol and soluble salts, such as sodium, potassium, calcium and magnesium chlorides.

The ophthalmic solutions of the present invention can include one or more non protein based surfactants. Suitable non protein based surfactants can include cationic, anionic, non-ionic or amphoteric surfactants suitable for use with the eye. Preferred non protein based surfactants are neutral or nonionic surfactants. Nonionic surfactants in accordance with the present invention include, but are not limited to, non-ionic block copolymers, preferably members of the group known as poly(oxyethylene)-poly(oxypropylene) block copolymers (also known as poloxamers) available under tradenames such as PLURONIC and EMKALYX. Poloxamers such as polyethyleneoxy-polypropyleneoxy block copolymer adducts of ethylene diamine (also known as poloxamine) are also suitable for use in the present invention (see, e.g. U.S. Pat. No. 4,820,352). Additional non protein-based surfactants include, but are not limited to, polyethylene glycol esters of fatty acids, polyoxypropylene ethers of $C_{12}$-$C_{18}$ alkanes and polyoxyethylene, polyoxypropylene block copolymers of ethylene diamine, poloxamer 182LF, poloxamer 188, poloxamer 331, poloxamer 407NF, sodium lauryl sulfate, pluronic F-127, Povidone (Sigma), PVP k-30, hydroxyethyl cellulose, NF and Tyloxapol (Sigma).

The non protein based surfactant, when present, is preferably in a concentration that ranges from about 0.01 to about 3 wt %, more preferably from about 0.1 to about 1.5 wt %, and most preferably from about 0.25 to about 0.5 wt %. Where used, the non protein based surfactant can include a single surfactant or a combination or surfactants.

The ophthalmic solutions of the present invention can further include various other known components which are generally used for cleaning and maintenance of contact lenses as long as the components are compatible with the antimicrobial activity of the collectins present in the solution. For example, the solutions can contain an enzyme component, an oxidative disinfectant component and/or a non-oxidative disinfectant component. Examples of suitable non-oxidative disinfectant components include, but are not limited to, tromethamine, polyhexamethylene biguanide, N-alkyl-2-pyrrolidone, chlorhexidine, polyquarternium-1, hexetidine, bronopol, alexidine, very low concentrations of peroxide, and ophthalmically acceptable salts thereof. The non-oxidative disinfectants for use in the present invention are preferably present in the liquid aqueous medium in concentrations in the range of about 0.00001 wt % to about 2 wt %.

Compositions of the present invention can also include one or more cation chelating agents. Chelating agents can improve the shelf-life of the ophthalmic solution. Chelating agents are well known to those of skill in the art. Preferred chelating agents include, but are not limited to, ethylenediaminetetraacetic acid (EDTA) and its salts (e.g., disodium), ethylenebis(oxyethylenenitrilo)tetraacetic acid (EGTA), and 2,2'-(ethylenediimino)-dibutyric acid EDBA which are preferably employed in amounts from about 0.01 to about 0.2 wt %, more preferably from about 0.1-0.2 wt %, and most preferably about 0.025 to about 2.0% wt %.

In certain embodiments, the ophthalmic solutions of this invention can optionally include one or more species of divalent cation. Exemplary divalent cations include, but are not limited to $Mg^{2+}$, $Ca^{2+}$, $Zn^{2+}$, $Fe^{2+}$, and $Ba^{2+}$, with $Mg^{2+}$ being most preferred. The divale when present, is at a concentration ranging from about 20 mM to about 50 mM.

In some embodiments of the present invention, a preservative can be added for the purpose of preserving the compositions. If used, preservatives are preferably in the range of, for example, about 0.0001 wt % to about 2.5 wt % of the composition, more preferably from about 0.1 wt % to about 1.0 wt %, and most preferably from about 0.2 wt % to about 0.5 wt %. Suitable preservatives include, but are not limited to chlorhexidine, thimerosal, PHMB (polyhexamethylene biguanide), boric acid, borate salts, potassium sorbate and sodium sorbate, benzalkonium chloride and other quaternary ammonium salt, guanidine salt such as chlorhexidine and polyhexamethylene biguanide, or formaldehyde donor, benzalkonium chloride, benzethonium chloride, benzoic acid, benzyl alcohol, butylparaben, cetylpyridinium chloride, chlorobutanol, chlorocresol, cresol, dehydroacetic acid, ethylparaben, methylparaben, methylparaben sodium, phenol, phenylethyl alcohol, phenylmercuric acetate, phenylmercuric nitrate, polyquad, potassium benzoate, propylparaben, propylparaben sodium, sodium benzoate, sodium dehydroacetate, sodium propionate, sorbic acid, sodium perborate, thymol, and antimicrobial polypeptides (e.g., a crecropin, a defensin, and a magainin), and mixtures thereof.

The ophthalmic solutions of the present invention can further include a demulcent, e.g., a water-soluble polymer that protects and lubricates mucous membrane surfaces and relieves dryness and irritation when applied to the eye. Examples of suitable demulcents include, but are not limited to, polyvinyl alcohol, polyvinyl pyrrolidone, cellulose derivatives, polyethylene glycol, propylene glycol, polysorbate 80, polyvinyl pyrrolidone, polyethylene oxide, polystyrene sulfonate, polyacrylamide, hydroxy ethyl cellulose, polyethylene glycol 6000, dextrose, and glycerin. The use of various demulcents are know to those of skill in the art (see U.S. Pat. Nos. 5,591,426, 5,106,615, 4,029,817, 3,767,788; 3,767,789; 3,856,919; 3,907,985; 3,920,810; 3,947,573; 3,987,163, 3,549,747, 4,131,651, 4,120,949, and 4,409,205, each of which is incorporated by reference herein in its entirety and for all purposes).

In another embodiment, the ophthalmic solutions of this invention can optionally include viscosity adjusting agents. Suitable viscosity adjusting agents for administration to an eye are well known to those of skill in the art. Viscosity adjusting agents include, but are not limited to cellulose derivatives such as hydroxypropyl methyl cellulose, carboxymethyl cellulose, methyl cellulose, and hydroxyethyl cellulose. Particularly when used as an artificial tear, the ophthalmic solution preferably has a viscosity from about 1 to about 50 cps.

Methods of using contact lens cleaning solutions are well known. For example, the contact lens can be contacted with the ophthalmic composition containing one or more collectins or surfactant proteins for the desired length of time, rinsed (with either the ophthalmic solution or with saline), and inserted into the eye of the user.

In an alternative embodiment of the present invention, an antimicrobial lens comprising one or more collectins or surfactant proteins is provided. The collectins or surfactant proteins of the present invention can be added to lens formulations using known methods of incorporating antimicrobial agents into contact lenses. The proteins of the present invention can also be added to the packaging solution containing the lens.

Exemplary lens formulations include those soft contact lens formulations described in U.S. Pat. Nos. 5,710,302; 5,998,498; 6,087,415; 5,760,100; 5,776,999; 5,789,461; 5,849,811; 5,965,631; 5,998,498; 6,087,415; 5,760,100; 5,776,999; 5,789,461; 5,849,811; and 5,965,631, each of which is incorporated herein by reference in its entirety and for all purposes. Examples of commercially available soft contact lenses formulations include but are not limited to the formulations of etafilcon A, genfilcon A, lenefilcon A, polymacon, acquafilcon A, balafilcon A, and lotrafilcon A. The amount of collectins or surfactant protein contained in the soft contact lenses of the invention is preferably from about 0.01 wt % to about 20 wt %, more preferably, about 0.02 wt % to about 1.0 wt %.

Collectins and/or surfactant proteins can also be incorporated into hard contact lens. Hard contact lenses are made from polymers that include but are not limited to polymers of poly(methyl)methacrylate, silicon acrylates, fluoroacrylates, fluoroethers, polyacetylenes, and polyimides. Exemplary lens formulations include those described in JP 200010055, JP 6123860 and U.S. Pat. No. 4,330,383, each of which is incorporated herein by reference in its entirety and for all purposes. The amount of collectins or surfactant protein contained in the hard contact lenses of the invention is preferably, from about 0.01 wt % to about 20 wt %, more preferably, about 0.02 wt % to about 1.0 wt %.

Intraocular lenses comprising collectins and/or surfactant proteins of the present invention can be formed using known materials. For example, the lenses can be made from a rigid material including, but not limited to, polymethyl methacrylate, polystyrene, polycarbonate, and combinations thereof. Additionally, flexible materials can be used including, but not limited to, hydrogels, silicone materials, acrylic materials, fluorocarbon materials or combinations thereof. Exemplary intraocular lenses are described in WO Publication Numbers 0026698, 0022460, 9929750, 9927978, and 0022459 and in U.S. Pat. Nos. 4,301,012; 4,872,876; 4,863,464; 4,725,277; 4,731,079, each of which is incorporated herein by reference in its entirety and for all purposes. The amount of collectins or surfactant protein contained in the intraocular lenses of the invention is preferably from about 0.01 wt % to about 20 wt %, more preferably, about 0.02 wt % to about 1.0 wt %.

The on-eye movement as well as the oxygen permeability of the lenses are factors to consider when preparing contact lens of the present invention. Oxygen permeability of a lens and oxygen transmissibility of lens material can be determined by methods disclosed in U.S. Pat. No. 5,849,811, incorporated herein by reference in its entirety and for all purposes. Methods of determining the on-eye movement of a lens are described in Young, G. et al., Influence of Soft Contact Lens Design on Clinical Performance, Optometry and Vision Science, 70(5):394-403. The amount of collectin or surfactant protein contained in the lenses of the present invention will depend on the amount of collectin or surfactant protein necessary to create a desired effect while not comprising both permeability and the shape and comfort, i.e., the fit, of the lens.

D. Kits

After a pharmaceutical comprising a collectin or surfactant protein has been formulated in a suitable carrier, it can be placed in an appropriate container and labeled for treatment of an indicated ocular disease. Additionally, another pharmaceutical comprising at least one other therapeutic agent useful in the treatment of ocular disease can be placed in the container as well and labeled for treatment of the indicated ocular disease. Alternatively, a single pharmaceutical comprising a collectin or surfactant protein and at least one other therapeutic agent useful in the treatment of an ocular disease can be placed in an appropriate container and labeled for treatment of an indicated disease. For administration of pharmaceuticals comprising collectins or surfactant proteins and of pharmaceuticals comprising, in a single pharmaceutical, collectins or surfactant proteins and at least one other therapeutic agent useful in the treatment of an ocular disease, such labeling would include, for example, instructions concerning the amount, frequency and method of administration. Similarly, for administration of multiple pharmaceuticals provided in the container, such labeling would include, for example, instructions concerning the amount, frequency and method of administration of each pharmaceutical.

In one embodiment, the invention provides for a kit for the treatment of an ocular disease, which includes a collectin and instructional materials teaching the indications, dosage, and schedule of administration of the collectin. When SP-D is the collectin provided in the kit, the instructional material indicates that SP-D can be used in a daily amount of between about 1 µg to about 1 mg and the administration continues for a period of about 21 days or less.

EXAMPLES

Example 1

Bacterial Strains and Preparation of Inocula

Six $P.$ $aeruginosa$ isolates were used. One of these isolates (strain 6206, serogroup O11) was classified as cytotoxic because it possesses the exoU gene and can induce acute cytotoxic effects on corneal epithelial cells. The other five strains were classified as invasive: they lack the exoU gene, and invade corneal epithelial cells. Invasive strains 6294 and 6487 (serogroup O6) are corneal isolates, PAK (serogroup O1) is a bacteremic isolate, while PAO1 (serogroup O2) and PA1244 (serogroup O7) are laboratory strains. All of the bacteria demonstrated flagella-mediated motility.

Bacterial inocula were prepared from overnight cultures grown on Trypticase soy agar (TSA) plates at 37° C. before suspension in Minimal Essential Eagle Medium with Hank's salts and L-glutamine (Sigma, St Louis, Mo.) buffered with 1 M HEPES-NaOH (pH 7.6), 0.35 g of NaHCO3, and 6 g of bovine serum albumin (Sigma) per litre (MEM). The bacteria were initially prepared to a concentration of $10^8$ cfu bacteria /ml MEM as determined by spectrophotometry (optical density of 0.1 at 650 nm). The bacterial suspension was then diluted to a concentration of $10^6$/ml in either MEM or whole tear fluid for use in experiments. Bacterial numbers were confirmed by viable counts after serial dilution.

Example 2

Tear Collection

Tear film was collected from the lower conjunctival sac of human subjects by the use of capillary tubes as approved by the Committee for the Protection of Human Subjects, University of California, Berkeley, Calif. A tear volume of 100 µl was collected over approximately 15 min on each occasion. The collected tears were pooled, aliquoted, and frozen (−20° C.) until used in experiments. The same batch of pooled tears was used in all experiments.

Example 3

Cell Cultures

Rabbit corneal epithelial cells were cultured in 96-well tissue culture plates (Becton Dickinson, Franklin Lake, NJ) in the presence of SHEM medium. Cells were fed on alternate days and used for experiments 4-6 days after passaging. Prior to each experiment, wells containing cultured cells were washed once with 100 µl phosphate buffered saline (PBS) to remove residual SHEM and antibiotics.

Example 4

Bacterial Growth Assays

The effect of tear fluid on bacterial growth and viability was tested with and without the presence of corneal epithelial cells. This was done by adding 40 µl of bacterial suspension, in either MEM or tear fluid, to empty wells of tissue culture dishes or to wells containing corneal epithelial cell cultures. Following a 3-h incubation at 37° C., 5 µl of bacterial suspension was collected for quantification by viable counting after serial dilution. The number of bacteria present in each well at the end of the experiment was compared to the starting inoculum to study bacterial growth/killing.

Figure 1B:
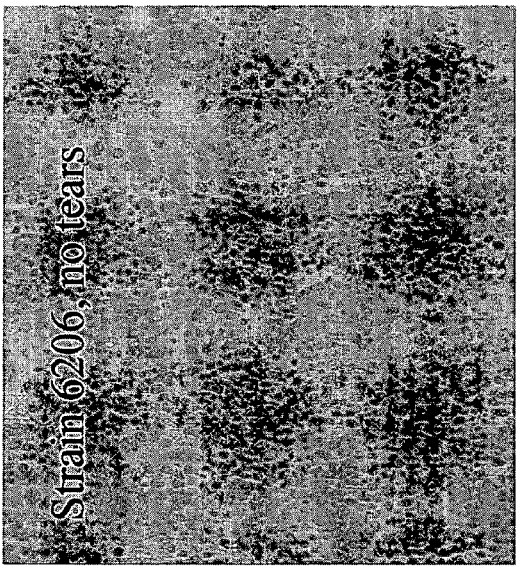
FIG. 1B shows quantification of bacterial-induced cell damage by measuring lactate dehydrogenase (LDH) release from dead or damaged corneal epithelial cells. Trypan blue staining and LDH release assays each show that whole human tear fluid protects corneal cells from cytotoxic activity of *P. aeruginosa* strain 6206.

Bacterial-induced cell damage was quantified by measuring lactate dehydrogenase (LDH) release from dead or damaged cells (see FIG. 1). Wells containing cultured cells were inoculated with 40 µl of MEM or tear fluid containing $10^6$ cfu/ml of cytotoxic $P.$ $aeruginosa$. After a 3 h incubation at 37° C., the supernatant from each well was collected and diluted 1:20 with fresh MEM. The quantity of LDH in the samples was detected by using a Cytotoxicity Detection Kit (Roche Diagnostics, Indianapolis, Ind.) according to manufacturer's instructions, and expressed as absorbance at 490 nm. An additional two sets of wells were treated with MEM without bacteria. One set of cells was used to determine background LDH release, while cells in the other group were lysed with MEM containing Triton-X 100 (0.25% vol/vol) (LabChem Inc., Pittsburgh, Pa.) at the end of assay to determine the amount of LDH released when 100% of the cells are killed. Trypan blue exclusion assays were also used to qualitatively assess the pattern of corneal cell death (see FIG. 1). Bacterial suspensions were removed after the 3-h incubation (above), and cells were washed once with PBS (50 µl) prior to treatment with MEM (100 µl) containing gentamicin (200 µg/ml) (Biowhittaker, Walkersville, Md.) for 1 h at 37° C. to kill extracellular bacteria. This was done to match the methods used for invasion assays described below, and to prevent the progression of cytotoxicity beyond the 3 h incubation period. Cells were washed with 100 µl PBS before addition of 100 µl Trypan blue solution (0.04% wt/vol) for 15 min to stain dead or dying cells. The trypan blue solution was then replaced with 50 µl HAM's F-12 medium (Biowhittaker, Walkersville, Md.), and the center of each well photographed using an Olympus IX70 inverted light microscope (10× objective, 10× ocular) attached to a video camera (Optronics, Goleta, Calif.) and computer-based imaging system (Inovision, Raleigh, N.C.).

Example 5

Bacterial Invasion Assays

Bacterial invasion of corneal epithelial cells was quantified using gentamicin survival assays. Cells were incubated with an invasive $P.$ $aeruginosa$ strain (3 h, 37° C.) prior to treatment with gentamicin to kill extracellular bacteria as described above for cytotoxicity assays. After washing to remove the antibiotic, cells were lysed by exposure to PBS containing Triton X-100 (0.25% vol/vol) for 15 min. Viable counts were then performed on the lysate to quantify the previously intracellular bacteria (see FIG. 2).

Example 6

In Vivo Model of Corneal Infection

After anesthesia, three linear scratches were applied to one cornea of female C57BL/6 mice using a sterile 25-gauge needle, and then the scratches were allowed to heal for 0, 6, 9, or 12 h. Animals were infected with $10^6$-$10^8$ cfu bacteria in 5 µl buffered MEM. At least three animals were assigned to each experimental group for each experiment. At 1, 2, 4, 7, and 14 days post-bacterial challenge, corneal disease was scored in masked fashion using two different grading systems. The overall severity of infections was scored as follows: Grade 0, eye macroscopically identical to the uninfected control eye; Grade 1, faint opacity partially covering the pupil; Grade 2, dense opacity covering the pupil; Grade 3, dense opacity covering the entire anterior segment; Grade 4, perforation of the cornea and/or phthisis bulbi (shrinkage of the eyeball). An eye receiving an overall grade of 2 or greater was considered infected. Another 5-point grading system (grade 0=no infection to grade 4=severe infection) that assesses four different characteristics of the disease was also used. This involved scoring the area and the density of the central opacity, the density of peripheral opacity, and the epithelial surface quality. The calculated sum of scores for these four characteristics ranges from a possible 0 (clear, normal) to a maximum of 16. Descriptive comments were also recorded and eyes were photodocumented using an Optronics 3-chip cooled camera (Goleta, Calif.) attached to a Zeiss Stemi 2000-C dissecting microscope (Jena, Germany). All experiments were repeated at least twice, and all procedures were done in accordance with the Association for Research in Vision and Ophthalmology Statement for the Use of Animals in Ophthalmic and Vision Research and were approved by the U.C. Berkeley Animal Care and Use Committee.

Example 7

ELISA for Quantitation of SP-D in Tears

The reagents were as follows: Plates: Flexible polyvinyl ELISA plates from Dynatech; these bind mannan much better than hard plastic does. Diluent: Since binding of SP-D to mannan is $Ca^{2+}$-dependent, diluent is TBS-rather than PBS-based so that $Ca^{2+}$ can be added. Mannan was obtained from *Saccharomyces cerevisae* (Sigma Cat.#M-7504). Recombinant human SP-D (30.5 µg/ml in TBS+10 mM $CaCl_2$), and rabbit anti-human SP-D antibody were obtained previously by Dr. Anders (Department of Microbiology and Immunology, University of Melbourne, Australia) as a gift from Dr. Erika Crouch (Washington University School of Medicine, St. Louis, Mo., USA).

The assay was conducted at room temperature in a humidified atmosphere. The wells were coated overnight with 50 µl mannan (100 µg/ml in TBS or PBS, pH7.2), then aspirated, and blocked with 150 µl BSA (10 mg/ml in TBS or PBS). The BSA was aspirated, and the wells washed 5× with TBST (TBS containing 0.05% Tween-20). For each sample, serial two-fold dilutions were prepared across 8 wells of the plate, 50 µl per well, in (i) $BSA_5$-TBST-Ca (TBS containing 5 mg BSA/ml, 0.05% Tween 20 and 5 mM $CaCl_2$) and (ii) $BSA_5$-TBST-EDTA (TBS containing 5 mg BSA/ml, 0.05% Tween 20 and 5 mM EDTA). Titrations of recombinant human SP-D were included for use as standard curve, starting at 2 µg/ml in first well. The plate was incubated overnight. Rows of wells were aspirated from the lowest concentration up, then washed 5× with TBST. (NOTE: from here on the diluent is $BSA_5$-TBST-Ca only).

Figure 3:
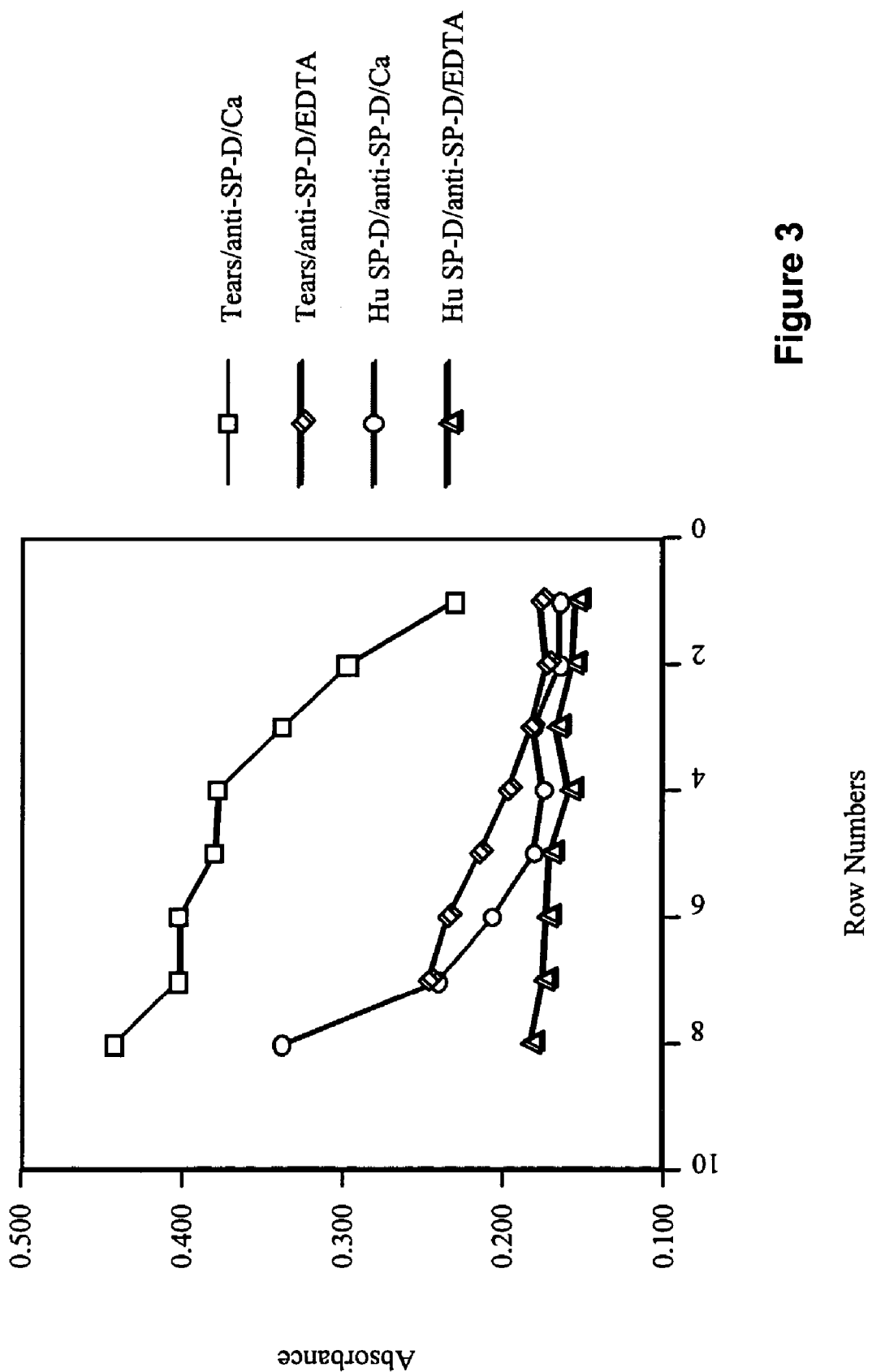
FIG. 3: Examination of human tear fluid by ELISA using anti-SP-D antibody. The graph demonstrates that human tears contain significant amounts of SP-D.

50 µl rabbit anti-SP-D serum (1/400 dilution in $BSA_5$-TBST-Ca). was added to each well, and incubated 3-4 h at room temp. The wells were aspirated then washed 5× with TBST. 50 µl HRPO-conjugated swine anti-rabbit Ig (Dako; 1/400 dilution in $BSA_5$-TBST-Ca) was the added to each well, and incubated 1 h at room temperature. The above wash was repeated. 100 µl substrate [ABTS=2,2'-azino-bis (3-ethylbenzthiazoline-6-sulfonic acid) (0.2 mM in 50 mM citrate buffer, pH 4.0, containing 0.004% $H_2O_2$)] was added to each well. After ~20 min (or when appropriate) color development was stopped by adding 50 µl sodium fluoride (NaF, stock at 192 mg/ml in water) to wells. Absorbance at dual wavelengths of 405/450 nm was read. Concentration of SP-D in sample was determined by reference to standard curve. (see FIG. 3).

Example 8

Adsorption of SP-D from Human Tear Fluid with Mannan-Sepharose

Mannan was coupled to CNBr-Sepharose-4B following manufacturer's instructions. For example, 3.5 g washed CNBr Sepharose (gives about 12 ml swollen gel) was mixed with ~0.3 g mannan in 15-20 ml coupling buffer. To follow degree of coupling achieved, 2 ml sample of slurry was taken at t=0, then centrifuged to pellet gel (pellet gently by bringing centrifuge up to 1000 rpm then immediately switch off without brake). The $E_{280}$ of the supernatant was measured against coupling buffer as blank. The beads were gently resuspended and returned to the main mixture, rotated end-over-end at room temperature for 2 h then overnight at 4° C. The mix was sampled again as before, and the absorbance read (t=18 h).

$$\frac{E_{280}(t=0) - E_{280}(t=18)}{E_{280}(t=0)} \times 100 = \% \text{ of original weight of mannan bound.}$$

From this, amount of mannan coupled can be calculated. The aim was to achieve ~8-12 mg mannan per ml of swollen gel $$\text{(for example: } \frac{0.555 - 0.321}{0.555} = 42.1\% \text{ of 250 mg}$$

$$= 105 \text{ mg mannan bound by 12 ml gel}$$

$$= 8.75 \text{ mg mannan/ml gel}$$

Excess mannan was washed away, and this was followed by blocking with Tris-HCl buffer (0.1 M, pH 8) for 2 h at room temperature, as in manufacturer's instructions, then washing with 3 cycles of alternating pH 4 (Acetate-buffered saline) and pH 8 (Tris-buffered saline), as per instructions. The gel was stored in the final wash buffer [Tris buffer (0.1M, pH 8) containing NaCl (0.5 M)] at 4° C., with 0.1% sodium azide.

SP-D adsorption procedure: Since TBS adversely affected corneal epithelial cells, complement fixation test buffer (veronal buffered saline, VBS), which was not toxic, was used as diluent in adsorption of tears with mannan-Sepharose. Veronal buffered saline—for 1 liter: Barbitone, 0.575 g; NaCl, 8.5 g; $MgCl_2.6H_2O$, 0.358 g; $CaCl_2.2H_2O$ 0.037 g; Barbitone sodium 0.185 g; pH 7.2; filter sterilize.

This recipe contains 0.25 mM $Ca^{++}$. For use in adsorption experiments, it was supplemented with an additional 10 mM $CaCl_2$.

Human tear fluid was adsorbed with an equal volume of packed washed mannan-Sepharose beads. The procedure resulted in a 1:2 dilution of the tears. Thus, for establishing an "unadsorbed" tears control, an aliquot of tears was also diluted 1:2 in VBS-10 mM $Ca^{++}$ (finally 5 mM $Ca^{++}$). For the adsorption: an aliquot of Mannan-Sepharose was washed 3× with VBS-10 mM $Ca^{++}$. Sufficient gel was used to give a pellet equal in volume to that of the tears to be treated. (Note: the washing procedure must be gentle, i.e., a short pulse spin to 1000 rpm, then brake off, as above). The supernatant was removed, and the gel pellet resuspended very gently in an equal volume of tears. This mix was then incubated on ice for 2 h, with occasional very gentle shaking.

Figure 4:
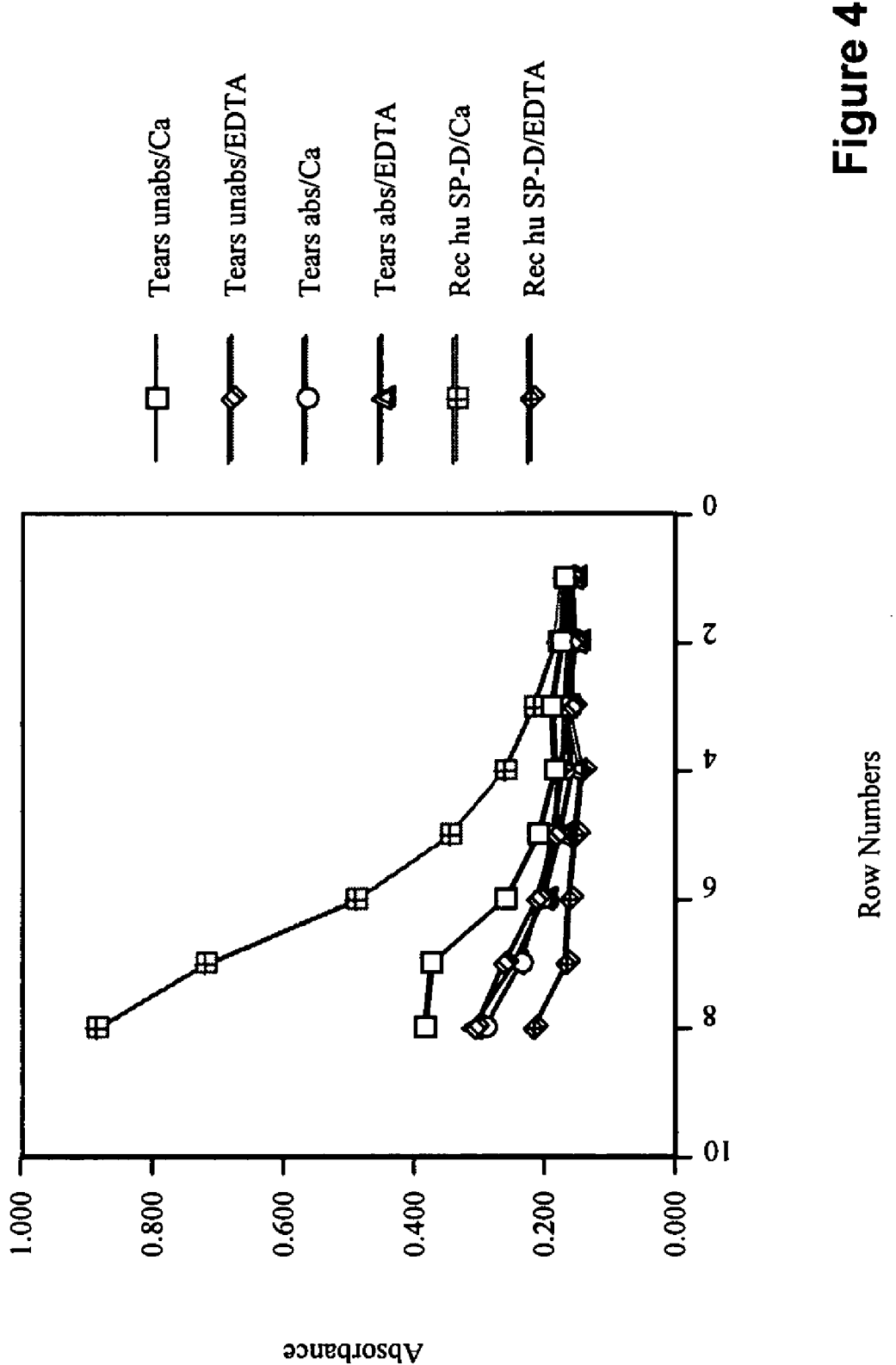
FIG. 4: Adsorption of SP-D from human tear fluid by ELISA with Mannan-Sepharose. The graph demonstrates that after adsorption with Mannan-Sepharose, SP-D was removed from human tears.
Figure 5:
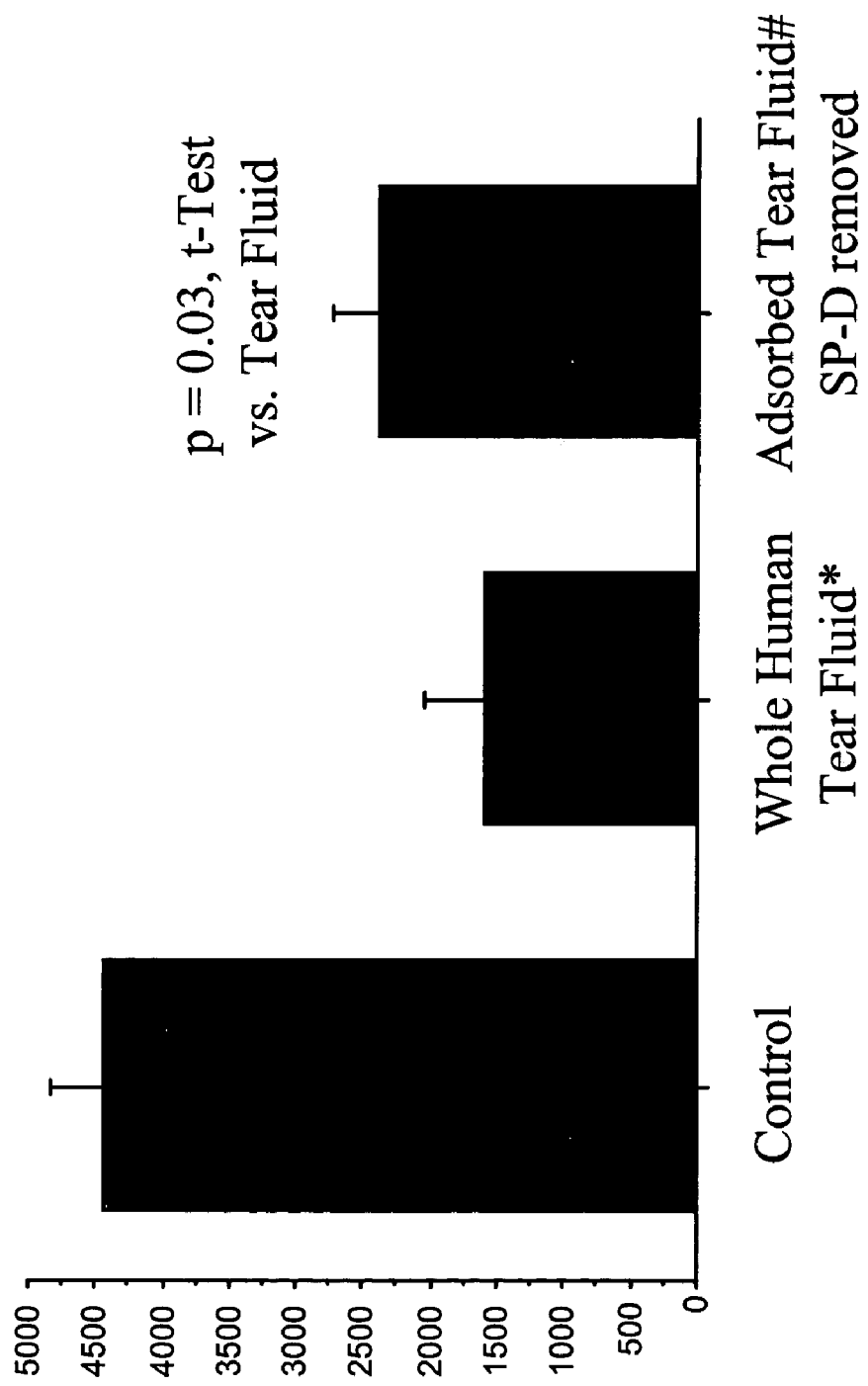
FIG. 5: SP-D adsorbed tears, a matched control of unadsorbed tears, and control buffer were tested for their ability to inhibit *P. aeruginosa* invasion of rabbit corneal epithelial cells using a gentamicin survival assay. Adsorption of SP-D from human tear fluid was achieved using mannan-conjugated sepharose, and the extent of SP-D removal was measured by ELISA. Bacterial strain=PAK, Inoculum~$10^6$ cfu/ml, Incubation time 3 h.
Figure 6:
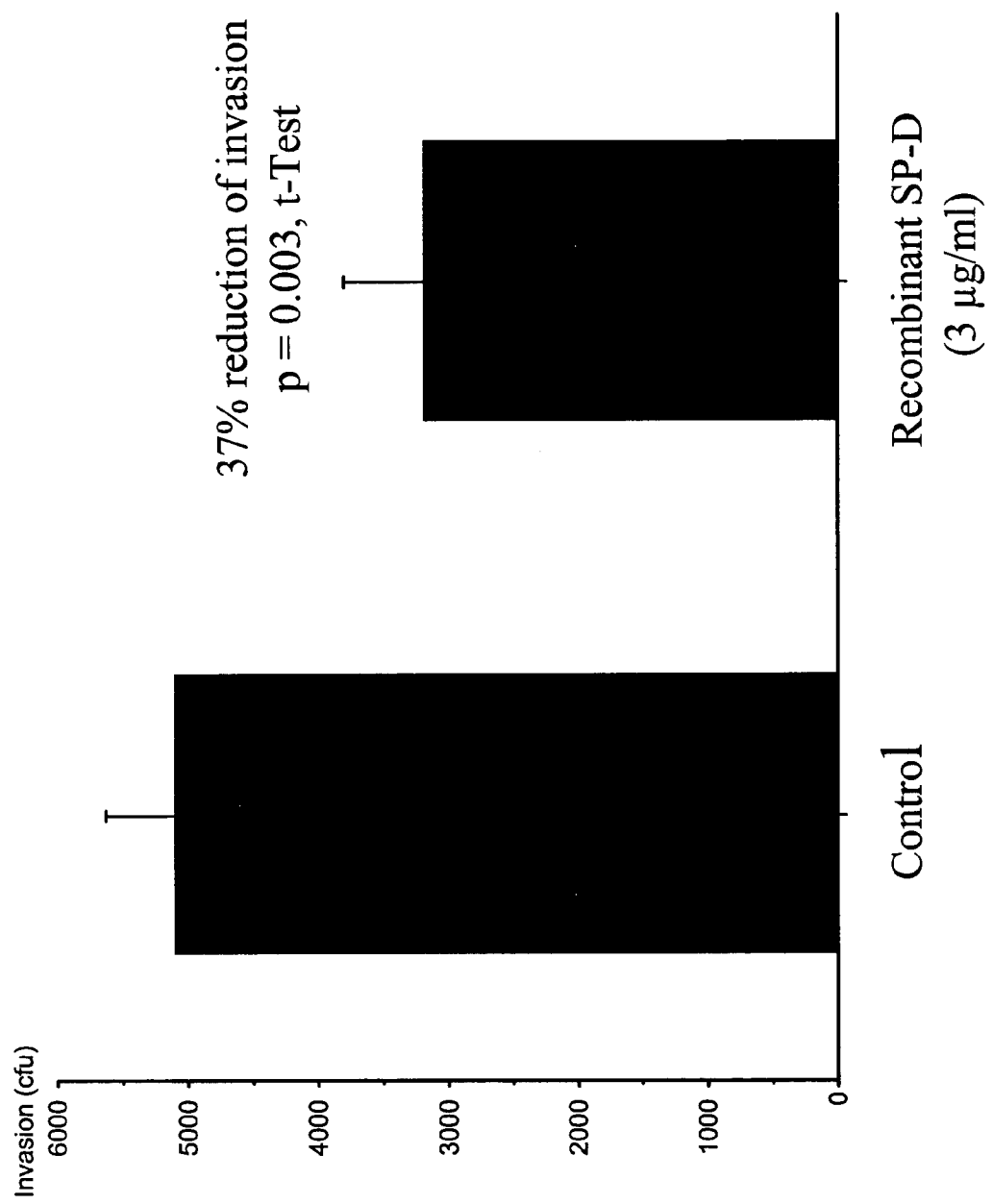
FIG. 6: A gentamicin survival assay was used to test if recombinant SP-D (3 ug/ml) could inhibit *P. aeruginosa* invasion of rabbit corneal epithelial cells. Recombinant SP-D or mock (stock buffer) control was added to bacterial inoculum to desired concentration immediately prior to addition to corneal cells.
Figure 7:
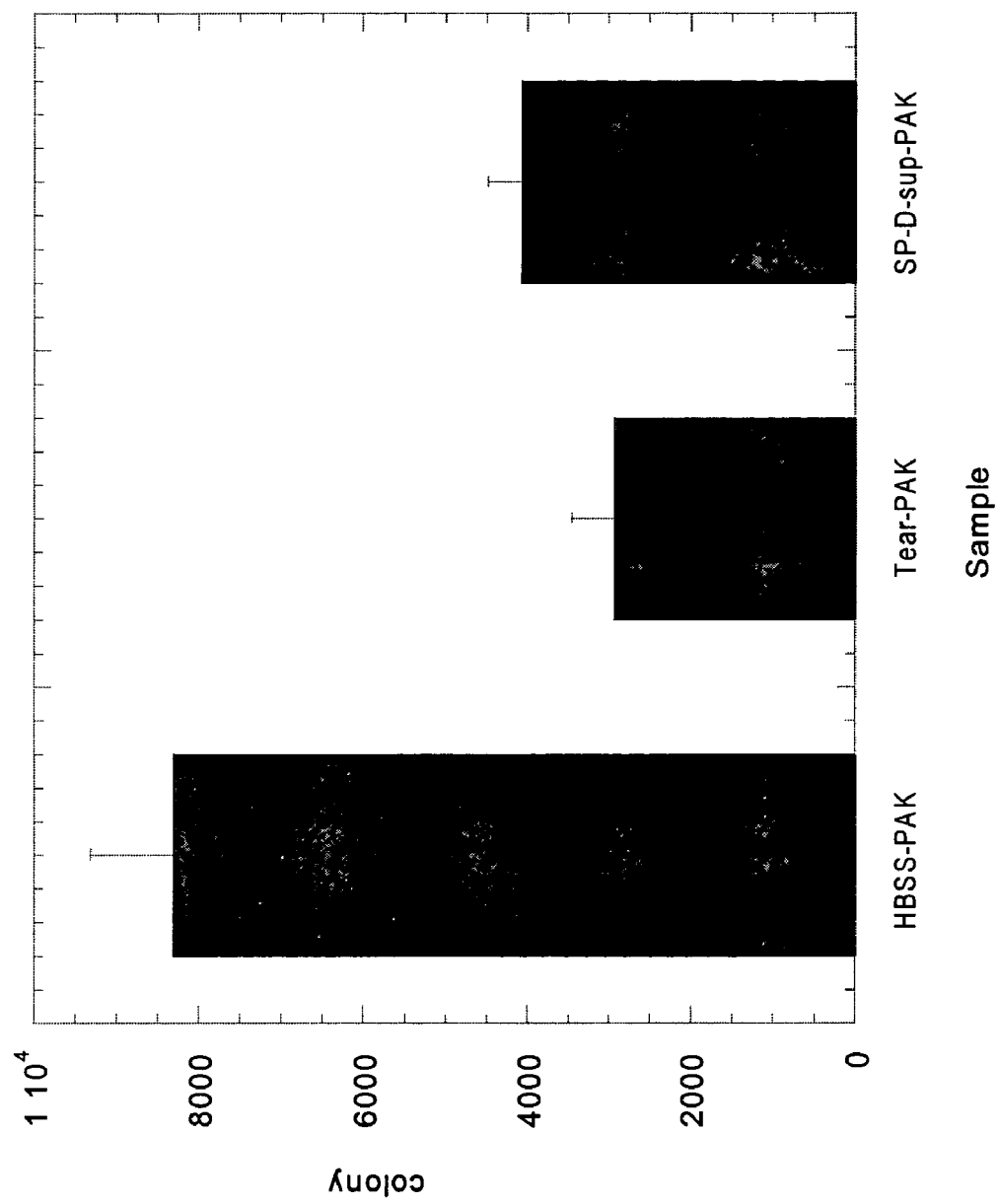
FIG. 7: SP-D was removed from human tear fluid by immunoprecipitation with anti-SP-D antibody. SP-D-sup tears (SP-D removed), a matched control of whole tears, and control buffer were tested for their ability to inhibit *P. aeruginosa* invasion of rabbit corneal epithelial cells using a gentamicin survival assay. Bacterial strain=PAK; HBSS=Hank's Balanced Salt Solution; Inoculum~$10^6$ cfu/ml, Incubation time 3 h.

The Mannan-Sepharose was centrifuged, then the supernatant centrifuged further in a microfuge (fast spin) to ensure supernatant is free of mannan-Sepharose beads. The supernatant was retained as the sample of absorbed tears, now at 1 in 2 dilution ($Ca^{++}$=5 mM). The samples were assayed for SP-D by ELISA as above. (see FIG. 4)

Although the foregoing invention has been described in detail by way of example for purposes of clarity of understanding, it will be apparent to the artisan that certain changes and modifications are comprehended by the disclosure and can be practiced without undue experimentation within the scope of the appended claims, which are presented by way of illustration not limitation.

All publications and patent documents cited above are hereby incorporated by reference in their entirety for all purposes to the same extent as if each were so individually denoted.

What is claimed:

1. A method for treating an ocular disease caused by a bacterial microbe in a subject, the method comprising administering into the eye of a subject, a pharmaceutical composition comprising a therapeutically effective amount of a surfactant protein-A or surfactant protein-D.

2. The method of claim 1, wherein said ocular disease is bacterial keratitis.

3. The method of claim 1, wherein said subject is a contact-lens wearer.

4. The method of claim 1, wherein said surfactant protein is applied topically.

5. The method of claim 1, further comprising administering a second therapeutic agent to said subject.

6. The method of claim 1 wherein said surfactant protein is surfactant protein-D.

7. The method of claim 1, wherein said microbe is a gram-negative bacterium.

8. The method of claim 7, wherein said gram-negative bacterium is *Pseudomonas aeruginosa*.

9. A method for treating an ocular disease caused by a bacterial microbe in a subject, the method comprising administering into the eye of a subject, a pharmaceutical composition comprising a therapeutically effective amount of a surfactant protein.

10. A method for reducing bacterial invasion of corneal cells, the method comprising administering into the eye of a subject, a pharmaceutical composition comprising a therapeutically effective amount of surfactant protein-D.

* * * * *